United States Patent
Chassot et al.

[11] Patent Number: 6,132,475
[45] Date of Patent: *Oct. 17, 2000

[54] DIAMINOBENZENE DERIVATIVE COMPOUNDS AND DYE COMPOSITIONS CONTAINING SAME

[75] Inventors: Laurent Chassot, Praroman; Hans-Juergen Braun, Ueberstorf, both of Switzerland

[73] Assignee: Wella Aktiengesellschaft, Darmstadt, Germany

[*] Notice: This patent is subject to a terminal disclaimer.

[21] Appl. No.: 09/250,314

[22] Filed: Feb. 15, 1999

[30] Foreign Application Priority Data

Mar. 19, 1998 [DE] Germany .......................... 198 12 058

[51] Int. Cl.[7] .......................... A61K 7/13; C07D 207/30; C07D 307/34; C07D 333/02; C07D 345/00

[52] U.S. Cl. .......................... 8/409; 8/407; 8/410; 8/411; 8/412; 8/416; 8/423; 8/574; 8/575; 8/577; 540/1; 548/561; 548/577; 549/74; 549/491; 549/505

[58] Field of Search .......................... 8/407, 408, 409, 8/410, 411, 412, 416, 423, 574, 575, 577; 540/1; 548/561, 577; 549/74, 80, 491, 505

[56] References Cited

U.S. PATENT DOCUMENTS

| | | | |
|---|---|---|---|
| 3,644,399 | 2/1972 | Brown et al. | 548/562 |
| 4,149,848 | 4/1979 | Bugaut et al. | 8/410 |
| 4,680,413 | 7/1987 | Genda et al. | 548/526 |
| 5,019,130 | 5/1991 | Flood | 8/423 |
| 5,851,237 | 12/1998 | Anderson et al. | 8/409 |
| 5,876,464 | 3/1999 | Lim et al. | 8/409 |
| 5,993,491 | 11/1999 | Lim et al. | 8/409 |

*Primary Examiner*—Caroline D. Liott
*Attorney, Agent, or Firm*—Michael J. Striker

[57] ABSTRACT

New p-diaminobenzene derivative compounds of the formula (I):

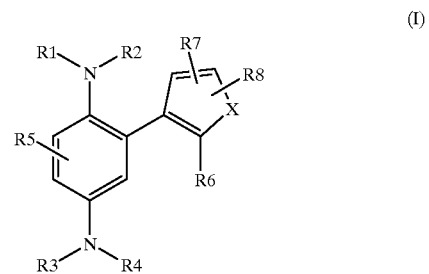

and physiologically compatible water soluble salts thereof are described, wherein X represents oxygen, sulfur, selenium or N-R9. Compositions for dyeing keratin fibers including a combination of coupler and developer substance are described, in which the developer substance includes at least one of the new p-diaminobenzene derivative compounds.

17 Claims, No Drawings

DIAMINOBENZENE DERIVATIVE COMPOUNDS AND DYE COMPOSITIONS CONTAINING SAME

BACKGROUND OF THE INVENTION

The present invention relates to new p-diaminobenzene derivative compounds and compositions for dyeing keratin fibers containing these new compounds.

Oxidation dye compounds have long attained substantial importance in the art of dyeing keratin fibers, especially hair dyeing. The dyeing caused by those compounds occurs by reaction of certain developer substances with certain coupler substances in the presence of a suitable oxidizing agent. For example, 2,5-diaminotoluene, 2,5-diaminophenylethylalcohol, p-aminophenol and 1,4-diaminobenzene can be mentioned as developer substances, while resorcinol, 4-chlororesorcinol, 1-naphthol, 3-aminophenol and derivatives of m-phenylendiamine can be mentioned as coupler substances.

There are numerous additional requirements for oxidation dye compounds that are used to dye human hair besides the color of the desired intensity. Thus the dye compounds must be unobjectionable in regard to toxicological and dermatological properties and must provide the desired hair color with a good light fastness, fastness to a permanent wave treatment, acid fastness and fastness to rubbing. The color of the hair dyed with the dye compounds in each case must be stable for at least 4 to 6 weeks to light, rubbing and chemical agents. Furthermore an additional requirement is the production of a broad palette of different color shades using different developer and coupler substances.

It is not possible to fulfill all the above-mentioned requirements with the currently known dye compounds.

SUMMARY OF THE INVENTION

It is an object of the present invention to provide improved developer compounds that fulfill the above-described requirements in a special manner.

It has now been surprisingly found that the new p-diaminobenzene derivative compounds according to formula (I) fulfill the requirements for developer compounds to an especially great extent manner. Particularly bright or intense color shades are produced using these developer substances with predominantly known coupler substances, which are however extraordinarily light fast and fast to washing.

The subject matter of the present invention is thus p-diaminobenzene derivative compounds of the following formula (I), or their physiologically compatible water soluble salts:

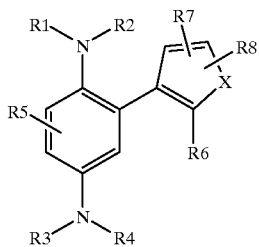

(I)

wherein X represents oxygen, sulfur, selenium or N-R9; R1, R2, R3 and R4 each, independently of each other, represents hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$)-alkyl group or R1 and R2 or R3 and R4 represent a four-membered to eight-membered aliphatic ring, with the proviso that at least 2 of the R1 to R4 groups represent hydrogen;

R5 represents hydrogen, a halogen atom, a $C_1$- to $C_4$-alkyl group, a $C_1$- to $C_4$-hydroxyalkyl group or a $C_1$- to $C_4$-alkoxy group;

R6 represents hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, an alkylamino group, a dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydroxyalkyl group, a —CH=CHR10 group, a —(CH$_2$)$_p$—CO$_2$R11 group or a —(CH$_2$)$_p$R12 group with p=1, 2, 3 or 4, a —C(R13)=NR14 group or a —C(R16)H—NR17R18 group;

R7 and R8 each, independently of each other, represents hydrogen, a halogen atom, a cyano group, a hydroxy group, a $C_1$- to $C_4$-alkoxy group, a $C_1$- to $C_6$-alkyl group, a $C_1$- to $C_4$-alkylthioether group, a mercapto group, a nitro group, an amino group, an alkylamino group, a dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydroxyalkyl group, a —CH=CHR10 group, a —(CH$_2$)$_p$—CO$_2$R11 group or a —(CH$_2$)$_p$R12 group with p=1, 2, 3 or 4, a —C(R13)=NR14 group or a —C(R16)H—NR17R18 group;

R9 represents hydrogen, a $C_1$- to $C_6$-alkyl group, a $C_1$- to $C_4$-hydroxyalkyl group, a phenyl group or an acetyl group;

R10 represents hydrogen, a hydroxy group, a nitro group, an amino group, a —CO$_2$R11 or a —C(O)CH$_3$ group;

R11, R13 and R16 each, independently of each other, represents hydrogen or a $C_1$- to $C_4$-alkyl group;

R12 represents an amino group or a nitrile group;

R14, R17 and R18 each, independently of each other, represents hydrogen, a hydroxy group, a $C_1$- to $C_4$-alkyl group a $C_1$- to $C_4$-hydroxyalkyl group, a $C_3$- to $C_4$-dihydroxyalkyl group or a group of formula (II):

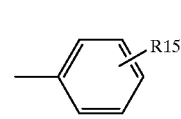

(II)

and

R15 represents hydrogen, an amino group or a hydroxy group.

The compounds of formula (I) can be, for example: 2,5-diamino-(3-thienyl)benzene; 2-amino-5-methylamino-(3-thienyl) benzene; 5-amino-2-methylamino-(3-thienyl) benzene; 2-amino-5-dimethylamino-(3-thienyl)benzene; 5-amino-2-dimethylamino-(3-thienyl)benzene; 2-amino-5-(2-hydroxyethyl)amino-(3-thienyl)benzene; 5-amino-2-(2-hydroxyethyl)amino-(3-thienyl)benzene; 2-amino-5-di(2-hydroxyethyl)amino-(3-thienyl)benzene; 5-amino-2-di(2-hydroxyethyl)amino-(3-thienyl)benzene; 2-amino-5-(2-hydroxyethyl)-methylamino-(3-thienyl)benzene; 5-amino-2-(2-hydroxyethyl)-methylamino-(3-thienyl)benzene; 2-amino-5-(2,3-dihydroxypropyl)amino-(3-thienyl) benzene; 5-amino-2-(2,3-dihydroxypropyl)amino-(3- thienyl)benzene; 2-amino-5-di(2,3-dihydroxypropyl)amino-(3-thienyl)benzene; 5-amino-2-di(2,3-dihydroxypropyl) amino-(3-thienyl)benzene; 2-amino-5-(2,3-dihydroxypropyl)methylamino-(3-thienyl)benzene; 5-amino-2-(2,3-dihydroxypropyl)methylamino(3-thienyl) benzene; 2-amino-5-(2-methoxyethyl)amino-(3-thienyl) benzene; 5-amino-2-(2-methoxyethyl)amino-(3-thienyl) benzene; 2-amino-5-di(2-methoxyethyl)amino-(3-thienyl) benzene; 5-amino-2-di(2-methoxyethyl)amino-( 3-thienyl) benzene; 2-amino-5-(2-methoxyethyl)methylamino-(3-thienyl)benzene; 5-amino-2-(2-methoxyethyl)methylamino-(3-thienyl)benzene; 2-amino-5-methylamino-(3-furyl) benzene; 5-amino-2-methylamino-(3-furyl)benzene; 2-amino-5-dimethylamino-(3-furyl)benzene; 5-amino-2-dimethylamino-(3-furyl)benzene; 2-amino-5-(2-hydroxyethyl)amino-(3-furyl)benzene; 5-amino-2-(2-hydroxyethyl)amino-(3-furyl)benzene; 2-amino-5-di(2-hydroxyethyl)amino-(3-furyl)benzene; 5-amino-2-di(2-hydroxyethyl)amino-(3-furyl)benzene; 2-amino-5-(2-hydroxyethyl)methylamino-(3-furyl)benzene; 5-amino-2-(2-hydroxyethyl)methylamino-(3-furyl)benzene; 2-amino-5-(2,3-dihydroxypropyl)amino-(3-furyl)benzene; 5-amino-2-(2,3-dihydroxypropyl)amino-(3-furyl)benzene; 2-amino-5-di(2,3-dihydroxypropyl)amino-(3-furyl)benzene; 5-amino-2-di(2,3-dihydroxypropyl)amino-(3-furyl) benzene; 2-amino-5-(2,3-dihydroxypropyl)methylamino-(3-furyl)benzene; 5-amino-2-(2,3-dihydroxypropyl) methylamino-(3-furyl)benzene; 2-amino-5-(2-methoxyethyl)amino-(3-furyl)benzene; 5-amino-2-(2-methoxyethyl)amino-(3-furyl)benzene; 2-amino-5-di(2-methoxyethyl)amino-(3-furyl)benzene; 5-amino-2-di(2-methoxyethyl)amino-(3-furyl)benzene; 2-amino-5-(2-methoxyethyl)methylamino-(3-furyl)benzene; 5-amino-2-(2-methoxyethyl)methylamino-(3-furyl)benzene; 2-amino-5-methylamino(pyrrol-3-yl)benzene; 5-amino-2-methylamino-(pyrrol-3-yl)benzene; 2-amino-5-dimethylamino-(pyrrol-3-yl)benzene; 5-amino-2-dimethylamino-(pyrrol-3-yl)benzene; 2-amino-5-(2-hydroxyethyl)amino-(pyrrol-3-yl)benzene; 5-amino-2-(2-hydroxyethyl)amino-(pyrrol-3-yl)benzene; 2-amino-5-di(2-hydroxyethyl)amino-(pyrrol- 3-yl)benzene; 5-amino-2-di(2-hydroxyethyl)amino-(pyrrol-3yl)benzene; 2-amino-5-(2-hydroxyethyl)methylamino-(pyrrol-3-yl)benzene; 5-amino-2-(2-hydroxyethyl)methylamino-(pyrrol-3-yl)benzene; 2-amino-5(2,3-dihydroxypropyl)amino-(pyrrol-3-yl)benzene; 5-amino-2-(2,3-dihydroxypropyl)amino-(pyrrol-3-yl)benzene; 2-amino-5-di(2,3-dihydroxypropyl)-amino-(pyrrol-3-yl)benzene; 5-amino-2-di(2,3-dihydroxypropyl) amino-(pyrrol-3yl)benzene; 2-amino-5-(2,3-dihydroxypropyl)methylamino-(pyrrol-3-yl)benzene; 5-amino-2-(2,3-dihydroxypropyl)methylamino-(pyrrol-3-yl)benzene; 2-amino-5-(2-methoxyethyl)amino-(pyrrol-3-yl)benzene; 5-amino-2-(2-methoxyethyl)amino(pyrrol-3-yl) benzene; 2-amino-5-di(2-methoxyethyl)amino-(pyrrol-3-yl) benzene; 5-amino-2-di(2-methoxyethyl)amino(pyrrol-3-yl) benzene; 2-amino-5-(2-methoxyethyl)-methylamino(pyrrol-3-yl)benzene; 5-amino-2-(2-methoxyethyl)methylamino-(pyrrol-3-yl)benzene; 2-amino-5-methylamino-(1-methyl-1H-pyrrol-3-yl)benzene; 5-amino-2-methylamino-(1-methyl-1H-pyrrol-3-yl)benzene; 2-amino-5-dimethylamino-(1-methyl-1H-pyrrol-3-yl)benzene; 5-amino-2-dimethylamino(1-methyl-1H-pyrrol-3-yl) benzene; 2-amino-5-(2-hydroxyethyl)amino-(1-methyl-1H-pyrrol-3-yl)benzene; 5-amino-2-(2-hydroxyethyl)amino-(1-methyl-1H-pyrrol-3-yl)benzene; 2-amino-5-di(2-hydroxyethyl)amino-(1-methyl-1H-pyrrol-3-yl)benzene; 5-amino-2-di(2-hydroxyethyl)amino-(1-methyl-1H-pyrrol-3-yl)benzene; 2-amino-5-(2-hydroxyethyl)-methylamino-(1-methyl-1H- pyrrol-3-yl)benzene; 5-amino-2-(2-hydroxyethyl)methylamino-(1-methyl-1H-pyrrol-3-yl) benzene; 2-amino-5-(2,3-dihydroxypropyl)amino-( 1-methyl-1H-pyrrol-3-yl)benzene; 5-amino-2-(2,3-dihydroxypropyl)amino-(1-methyl-1H-pyrrol-3-yl)benzene; 2-amino-5-di(2,3-dihydroxypropyl)-amino-(1-methyl-1H-pyrrol-3-yl)benzene; 5-amino-2-di(2,3-dihydroxypropyl) amino-(1-methyl-1H-pyrrol-3-yl)benzene; 2-amino-5-(2,3-dihydroxypropyl)methylamino-(1-methyl-1H-pyrrol-3-yl) benzene; 5-amino-2-(2,3-dihydroxypropyl)methylamino-(1-methyl-1H-pyrrol-3-yl)benzene; 2-amino-5-(2-methoxyethyl)amino-(1-methyl-1H-pyrrol-3-yl)benzene; 5-amino-2-(2-methoxyethyl)amino-(1-methyl-1H-pyrrol-3-yl)benzene; 2-amino-5-di(2-methoxyethyl)amino-(1-methyl-1H-pyrrol-3-yl)benzene; 5-amino-2-di(2-methoxyethyl)amino-(1-methyl-1H-pyrrol-3-yl)benzene; 2-amino-5-(2-methoxyethyl)methylamino-(1-methyl-1H-pyrrol-3-yl)benzene; 5-amino-2-(2-methoxyethyl) methylamino-(1-methyl-1H-pyrrol-3-yl)benzene; 2,5-diamino-3-methyl-(3-thienyl)benzene; 2-amino-5-di(2-hydroxyethyl)amino-3-methyl(3-thienyl)benzene; 5-amino-2-di(2-hydroxyethyl)amino-3-methyl-(3-thienyl)benzene; 2,5-diamino-3-chloro-(3-thienyl)benzene; 2-amino-5-di(2-hydroxyethyl)amino-3-chloro-(3-thienyl)benzene; 5-amino-2-di(2-hydroxyethyl)amino-3-chloro-(3-thienyl)benzene; 2,5-diamino-4-methyl-(3-thienyl)benzene; 2-amino-5-di(2-hydroxyethyl)amino-4-methyl-(3-thienyl)benzene; 5-amino-2-di(2-hydroxyethyl)amino-4-methyl-(3-thienyl) benzene; 2,5-diamino-4-chloro-(3-thienyl)benzene; 2-amino-5-di(2-hydroxyethyl)amino-4-chloro-(3-thienyl) benzene; 5-amino-2-di(2-hydroxyethyl)amino-4-chloro-(3-thienyl)benzene; 2,5-diamino-5-methyl-(3-thienyl)benzene; 2-amino-5-di(2-hydroxyethyl)amino-5-methyl-(3 -thienyl) benzene; 5-amino-2-di(2-hydroxyethyl)amino-5-methyl-(3-thienyl)benzene; 2,5-diamino-5-chloro-(3-thienyl)benzene; 2-amino-5-di(2-hydroxyethyl)amino-5-chloro-(3-thienyl) benzene; 5-amino-2-di(2-hydroxyethyl)amino-5-chloro-(3-thienyl)benzene; 2,5-diamino-3-methyl-(3-furyl)benzene; 2-amino-5-di(2-hydroxyethyl)amino-3-methyl-(3-furyl)-benzene; 5-amino-2-di(2-hydroxyethyl)amino-3-methyl-(3-furyl)benzene; 2,5-diamino-3-chloro-(3-furyl)benzene; 2-amino-5-di(2-hydroxyethyl)-amino-3-chloro-(3-furyl) benzene; 5-amino-2-di(2-hydroxyethyl)amino-3-chloro-(3-furyl)benzene; 2,5-diamino-4-methyl-(3-furyl)-benzene; 2-amino-5-di(2-hydroxyethyl)amino-4-methyl-(3-furyl) benzene; 5-amino-2-di(2-hydroxyethyl)amino-4-methyl-(3-furyl)benzene; 2,5-diamino-4-chloro-(3-furyl)benzene; 2-amino-5-di(2-hydroxy-ethyl)amino-4-chloro-(3-furyl) benzene; 5-amino-2-di(2-hydroxyethyl)amino-4-chloro-(3-furyl)benzene; 2,5-diamino-5-methyl-(3-furyl)benzene; 2-amino-5-di(2-hydroxyethyl)-amino-5-methyl-(3-furyl) benzene; 5-amino-2-di(2-hydroxyethyl)-amino-5-methyl-(3-furyl)benzene; 2,5-diamino-5-chloro-(3-furyl)benzene; 2-amino-5-di(2-hydroxyethyl)amino-5-chloro-(3-furyl) benzene; 5-amino-2-di(2-hydroxyethyl)-amino-5-chloro-(3-furyl)benzene; 2,5-diamino-3-methyl-(pyrrol-3-yl)benzene; 2-amino-5-di(2-hydroxyethyl)amino-3-methyl-(pyrrol-3-yl) benzene; 5-amino-2-di(2-hydroxyethyl)amino-3-methyl-(pyrrol-3-yl)benzene; 2,5-diamino-3-chloro-(pyrrol-3-yl) benzene; 2-amino-5-di(2-hydroxyethyl)-amino-3-chloro-(pyrrol-3-yl)benzene; 5-amino-2-di(2-hydroxyethyl)amino-3-chloro-(pyrrol-3-yl)benzene; 2,5-diamino-4-methyl-(pyrrol-3-yl)benzene; 2-amino-5-di(2-hydroxyethyl)amino-4-methyl-(pyrrol-3-yl)benzene; 5-amino-2-di(2-hydroxyethyl)amino-4-methyl-(pyrrol-3-yl)benzene; 2,5-diamino-4-chloro-(pyrrol-3-yl)benzene; 2-amino-5-di(2- hydroxyethyl)-amino-4-chloro(pyrrol-3-yl)benzene; 5-amino-2-di(2-hydroxyethyl)amino-4-chloro-(pyrrol-3-yl) benzene; 2,5-diamino-5-methyl-(pyrrol-3-yl)benzene; 2-amino-5-di(2-hydroxyethyl)amino-5-methyl-(pyrrol-3-yl) benzene; 5-amino-2-di(2-hydroxyethyl)amino-5-methyl-(pyrrol-3-yl)benzene; 2,5-diamino-5-chloro-(pyrrol-3-yl) benzene; 2-amino-5-di(2-hydroxyethyl)amino-5-chloro-(pyrrol-3-yl)benzene; 5-amino-2-di(2-hydroxyethyl)amino-5-chloro-(pyrrol-3-yl)benzene; 2,5-diamino-3-methyl-(1-methyl-1H-pyrrol-3-yl)benzene; 2-amino-5-di(2-hydroxyethyl)amino-3-methyl-(1-methyl-1H-pyrrol-3-yl) benzene; 5-amino-2-di(2-hydroxyethyl)amino-3-methyl-(1-methyl-1H-pyrrol-3-yl)benzene;

2,5-diamino-3-chloro-(1-methyl-1H-pyrrol-3-yl) benzene; 2-amino-5-di(2-hydroxyethyl)amino-3-chloro-(1-methyl-1H-pyrrol-3-yl)benzene; 5-amino-2-di(2-hydroxyethyl)amino-3-chloro-(1-methyl-1H-pyrrol-3-yl) benzene; 2,5-diamino-4-methyl-(1-methyl-1H-pyrrol-3-yl) benzene; 2-amino-5-di(2-hydroxyethyl)amino-4-methyl-(1-methyl-1H-pyrrol-3-yl)benzene; 5-amino-2-di(2-hydroxyethyl)amino-4-methyl-(1-methyl-1H-pyrrol-3-yl) benzene; 2,5-diamino-4-chloro-(1-methyl-1H-pyrrol-3-yl) benzene; 2-amino-5-{di(2-hydroxyethyl)amino}-4-chloro-(1-methyl-1H-pyrrol-3-yl) benzene; 5-amino-2-di(2-hydroxyethyl)amino-4-chloro-(1-methyl-1H- pyrrol-3-yl) benzene; 2,5-diamino-5-methyl-(1-methyl-1H-pyrrol-3-yl) benzene; 2-amino-5-di(2 -hydroxyethyl)amino-5-methyl-(1-methyl-1H-pyrrol-3-yl) benzene; 5-amino-2-di(2-hydroxyethyl)amino-5-methyl-(1-methyl-1H-pyrrol-3-yl)-benzene; 2,5-diamino-5-chloro-(1-methyl-1H-pyrrol-3-yl) benzene; 2-amino-5-di(2-hydroxyethyl)amino-5-chloro-(1-methyl-1H-pyrrol-3-yl)benzene; 5-amino-2-di(2-hydroxyethyl)amino-5-chloro-(1-methyl-1H-pyrrol-3-yl) benzene; 2,5-diamino-(2-methyl-3-thienyl)benzene; 2-amino-5-di(2-hydroxyethyl)amino-(2-methyl-3-thienyl) benzene; 5-amino-2-di(2-hydroxyethyl)amino-(2-methyl-3-thienyl)benzene; 2,5-diamino-(2-methyl-3-furyl)benzene; 2-amino-5-di(2-hydroxyethyl)amino-(2-methyl-3-furyl) benzene; 5-amino-2-di(2-hydroxyethyl)amino-(2-methyl-3-furyl)benzene; 2,5-diamino-(4-methyl-3-thienyl)benzene; 2-amino-5-di-(2-hydroxyethyl)amino-(4-methyl-3-thienyl) benzene; 5-amino-2-di(2-hydroxyethyl)amino-(4-methyl-3-thienyl)benzene; 2,5-diamino-(4-methyl-3-furyl)benzene; 2-amino-5-di(2-hydroxyethyl)amino-(4-methyl-3-furyl) benzene; 5-amino-2-di(2-hydroxyethyl)amino-(4-methyl-3-furyl)benzene; 2,5-diamino-(5-methyl-3-thienyl)benzene; 2-amino-5-di(2-hydroxyethyl)-amino-(5-methyl-3-thienyl) benzene; 5-amino-2-di(2-hydroxyethyl)amino-(5-methyl-3-thienyl)benzene; 2,5-diamino-(5-methyl-3-furyl)benzene; 2-amino-5-di(2-hydroxyethyl)-amino-(5-methyl-3-furyl) benzene; 5-amino-2-di(2-hydroxyethyl)amino-(5-methyl-3-furyl)benzene; 2,5-diamino-(2-ethyl-3-thienyl)-benzene; 2-amino-5-di(2-hydroxyethyl)amino-(2-ethyl-3-thienyl) benzene; 5-amino-2-di(2-hydroxyethyl)amino-(2-ethyl-3-thienyl)benzene; 2,5-diamino-(2-ethyl-3-furyl)-benzene; 2 -amino-5-di(2-hydroxyethyl)amino-(2-ethyl-3-furyl) benzene; 5-amino-2-di(2-hydroxyethyl)amino-(2-ethyl-3-furyl)benzene; 2,5-diamino-(4-ethyl-3-thienyl)benzene; 2-amino-5- di(2-hydroxyethyl)amino-(4-ethyl-3-thienyl) benzene; 5-amino-2-di(2-hydroxyethyl)amino-(4-ethyl-3-thienyl)-benzene; 2,5-diamino-(4-ethyl-3-furyl)benzene; 2-amino-5-di(2-hydroxyethyl)amino-(4-ethyl-3-furyl) benzene; 5-amino-2-di(2-hydroxyethyl)amino-(4-ethyl-3-furyl)benzene; 2,5-diamino-(5-ethyl-3-thienyl)benzene; 2-amino-5-di(2-hydroxy-ethyl)amino-(5-ethyl-3-thienyl) benzene; 5-amino-2-di(2-hydroxyethyl)amino-(5-ethyl-3-thienyl)benzene; 2,5-diamino-(5-ethyl-3-furyl)benzene; 2-amino-5-di(2-hydroxyethyl)amino-(5-ethyl-3-furyl) benzene; 5-amino-2-di(2-hydroxyethyl)amino-(5-ethyl-3-furyl)benzene; 2,5-diamino-(2-dimethylamino-3-thienyl) benzene; 2-amino-5-di(2-hydroxyethyl)amino-(2-dimethylamino-3-thienyl)benzene; 5-amino-2-di(2-hydroxy-ethyl)amino-(2-dimethylamino-3-thienyl)benzene; 2,5-diamino-(2-dimethylamino-3-furyl)benzene; 2-amino-5-di(2-hydroxy-ethyl)amino-(2-dimethylamino-3-furyl) benzene; 5-amino-2-di(2-hydroxyethyl)amino-(2-dimethylamino-3-furyl)benzene; 2,5-diamino-(4-dimethylamino-3-thienyl)benzene; 2-amino-5-di(2-hydroxy-ethyl)amino-(4-dimethylamino-3-thienyl)benzene; 5-amino-2-di(2-hydroxyethyl)amino-(4-dimethylamino-3-thienyl)benzene; 2,5-diamino-(4-dimethyl-amino-3-furyl)-benzene; 2-amino-5-di(2-hydroxyethyl)amino-(4-dimethyl-amino-3-furyl)benzene; 5-amino-2-di(2-hydroxyethyl) amino-(4-dimethyl-amino-3-furyl)benzene; 2,5-diamino-(5-dimethyl-amino-3-thienyl)benzene; 2-amino-5 -di(2-hydroxyethyl)amino-(5-dimethylamino-3-thienyl)benzene; 5-amino-2-di(2-hydroxy-ethyl)amino-(5-dimethylamino-3-thienyl)benzene; 2,5-diamino-(5-dimethylamino-3-furyl)benzene; 2-amino-5-di(2-hydroxy-ethyl)amino-(5-dimethylamino-3-furyl)benzene; 5-amino-2-di(2-hydroxyethyl)amino-(5-dimethylamino-3-furyl)benzene; 2,5-diamino-(2-formyl-3-thienyl)benzene; 2-amino-5-di(2-hydroxyethyl)amino-(2-formyl-3-thienyl)benzene; 5-amino-2-di(2-hydroxyethyl)amino-(2-formyl-3-thienyl) benzene; 2,5-diamino-(2-formyl-3-furyl)benzene; 2-amino-5-di(2-hydroxyethyl)amino-(2-formyl-3-furyl)benzene; 5-amino-2-di(2-hydroxyethyl)amino-(2-formyl-3-furyl) benzene; 2,5-diamino-(4-formyl-3-thienyl)benzene; 2-amino-5-di(2-hydroxyethyl)amino-(4-formyl-3-thienyl) benzene; 5-amino-2-di(2-hydroxyethyl)amino-(4-formyl-3-thienyl)benzene; 2,5-diamino-(4-formyl-3-furyl)benzene; 2-amino-5-di(2-hydroxyethyl)amino-(4-formyl-3-furyl) benzene; 5-amino-2-di(2-hydroxyethyl)amino-(4-formyl-3-furyl)benzene; 2,5-diamino-(5-formyl-3-thienyl)benzene; 2-amino-5-di(2-hydroxyethyl)amino-(5-formyl-3-thienyl) benzene; 5-amino-2-di(2-hydroxyethyl)amino-(5-formyl-3-thienyl)benzene; 2,5-diamino-(5-formyl-3-furyl)benzene; 2-amino-5-di(2-hydroxyethyl)amino-(5-formyl-3-furyl) benzene; 5-amino-2-di(2-hydroxyethyl)amino-(5-formyl-3-furyl)benzene; 2,5-diamino-(2-acetyl-3-thienyl)benzene; 2-amino-5-di(2-hydroxy-ethyl)amino-(2-acetyl-3-thienyl) benzene; 5-amino-2-di(2-hydroxyethyl)amino-(2-acetyl-3-thienyl)benzene; 2,5-diamino-(2-acetyl-3-furyl)benzene; 2-amino-5-di(2-hydroxyethyl)-amino-(2-acetyl-3-furyl) benzene; 5-amino-2-di(2 -hydroxy-ethyl)amino-(2-acetyl-3-furyl)benzene; 2,5-diamino-(4-acetyl-3-thienyl)benzene; 2-amino-5-di(2-hydroxyethyl)amino-(4-acetyl-3-thienyl) benzene; 5-amino-2-di(2-hydroxyethyl)amino-(4-acetyl-3-thienyl)benzene; 2,5-diamino-(4-acetyl-3-furyl)benzene; 2-amino-5-di(2-hydroxyethyl)amino-(4-acetyl-3-furyl) benzene; 5-amino-2-di(2-hydroxyethyl)amino-(4-acetyl-3-furyl)benzene; 2,5-diamino(5-acetyl-3-thienyl)-benzene; 2-amino-5-di(2-hydroxyethyl)amino-(5-acetyl-3-thienyl) benzene; 5-amino-2-di(2-hydroxyethyl)amino-(5-acetyl-3-thienyl)benzene; 2,5-diamino-(5-acetyl-3-furyl)-benzene; 2-amino-5-di(2-hydroxyethyl)amino-(5-acetyl-3-furyl) benzene; 5-amino-2-di(2-hydroxyethyl)amino-(5-acetyl-3-furyl)benzene; 2,5-diamino-(2-aminomethyl-3-thienyl) benzene; 2-amino-5-di(2-hydroxyethyl)amino-(2-aminomethyl-3-thienyl)-benzene; 5-amino-2-di(2-hydroxyethyl)amino-(2-aminomethyl-3-thienyl)benzene; 2,5-diamino-(2-aminomethyl-3-furyl)benzene; 2-amino-5-di(2-hydroxyethyl)amino-(2-aminomethyl-3-furyl)-benzene; 5-amino-2-di(2-hydroxyethyl)amino-(2- aminomethyl-3-furyl)benzene; 2,5-diamino-(4-aminomethyl-3-thienyl)-benzene; 2-amino-5-di-(2-hydroxyethyl)amino-(4-aminomethyl-3-thienyl)benzene; 5-amino-2-di(2-hydroxyethyl)amino-(4-aminomethyl-3-thienyl)benzene; 2,5-diamino-(4-aminomethyl-3-furyl)benzene; 2-amino-5-di(2-hydroxyethyl)amino-(4-aminomethyl-3-furyl)benzene; 5-amino-2-di(2-hydroxyethyl)-amino-(4-aminomethyl-3-furyl)benzene; 2,5-diamino-(5-aminomethyl-3-thienyl)benzene; 2-amino-5-di(2-hydroxy-ethyl)amino-(5-aminomethyl-3-thienyl)benzene; 5-amino-2-di(2-hydroxyethyl)amino-(5-aminomethyl-3-thienyl)benzene; 2,5-diamino-(5-aminomethyl-3-furyl)benzene; 2-amino-5-di(2-hydroxyethyl)amino-(5-aminomethyl-3-furyl)benzene; 5-amino-2-di(2-hydroxyethyl)amino-(5-aminomethyl-3-furyl)benzene; 2,5-diamino-(2-(2-hydroxyethyl(imino))methylene-3-thienyl)benzene; 2-amino-5-di(2-hydroxyethyl)amino-(2-(2-hydroxyethyl(imino))methylen-3-thienyl)benzene; 5-amino-2-di(2-hydroxyethyl)amino-(2-(2-hydroxyethyl(imino))-methylen-3-thienyl)benzene; 2,5-diamino-(2-(2-hydroxyethyl(imino))methylen-3-furyl)benzene; 2-amino-5-di(2-hydroxy-ethyl)amino-(2-(2-hydroxyethyl(imino))methylen-3-furyl)benzene; 5-amino-2-di(2-hydroxyethyl)amino-(2-(2-hydroxy-ethyl(imino))methylen-3-furyl)benzene; 2,5-diamino-(4-(2-hydroxyethyl(imino))methylen-3-thienyl)benzene; 2-amino-5-di(2-hydroxyethyl)amino-(4-(2-hydroxyethyl(imino))methylen-3-thienyl)benzene; 5-amino-2-di(2-hydroxyethyl)amino-(4-(2-hydroxyethyl-(imino))methylen-3-thienyl)benzene; 2,5-diamino-(4-(2-hydroxyethyl-(imino))methylen-3-furyl)benzene; 2-amino-5-di(2-hydroxyethyl)-amino-(4-(2-hydroxyethyl(imino))methylen-3-furyl)benzene; 5-amino-2-di(2-hydroxyethyl)amino-(4-(2-hydroxyethyl(imino))methylen-3-furyl)benzene; 2,5-diamino-(5-(2-hydroxyethyl(imino))methylene-3-thienyl)benzene; 2-amino-5-di(2-hydroxyethyl)amino-(5-(2-hydroxyethyl(imino))methylen-3-thienyl)benzene; 5-amino-2-di(2-hydroxyethyl)amino-(5-(2-hydroxyethyl(imino))methylen-3-thienyl)benzene; 2,5-diamino-(5-(2-hydroxyethyl(imino))methylen-3-furyl)benzene; 2-amino-5-di(2-hydroxyethyl)amino-(5-(2-hydroxyethyl(imino))methylen-3-furyl)benzene and 5-amino-2-di(2-hydroxyethyl)amino-(5-(2-hydroxyethyl(imino))methylen-3-furyl)benzene.

Preferred compounds of formula (I) include those in which (i) one or more of the groups R5, R6, R7 and R8 are hydrogen and/or (ii) R1, R2, R3 and R4 are simultaneously hydrogen and/or (iii) R7 is hydrogen and R6 is hydrogen, —C(O)H, C(O)CH$_3$, C$_1$–C$_4$-alkyl or C$_1$–C$_4$-hydroxyalkyl (particularly R6=R7=hydrogen).

Particularly the following compounds are named: 2,5-diamino-1-(5-chloro-3-thienyl)benzene; 2,5-diamino-1-(3-furyl)benzene; 2,5-diamino-1-(2-acetyl-3-thienyl)benzene; 2,5-diamino-1-(pyrrol-3-yl)benzene; 2,5-diamino-1-(2-formyl-3-thienyl)benzene; 2,5-diamino-1-(4-formyl-3-thienyl)-benzene; 2,5-diamino-1-(2-formyl-3-furyl)benzene; 2,5-diamino-1-(4-formyl-3-furyl)benzene; 2,5-diamino-1-(5-methyl-3-thienyl)benzene, 2,5-diamino-1-(5-methyl-3-thienyl)benzene, 2,5-diamino-1-(4-(4-nitropropenyl)-3-thienyl)benzene, 2,5-diamino-1-(3-furyl)benzene, 2,5-diamino-1-(4-formyl-3-thienyl)benzene, 2,5-diamino-1-(4-(2-hydroxyethyl)aminomethyl-3-thienyl)benzene, 2,5-diamino-1-(4-pyrrolidino-methyl-3-thienyl)benzene, 2,5-diamino-1-(4-(dimethylaminoethyl)aminomethyl- 3-thienyl)benzene, 2,5-diamino-1-(4-(2-methoxy-5-chlorophenyl)aminomethyl-3-thienyl)-benzene, 2,5-diamino-1-(4-(3-ethoxypropyl)-aminomethyl-3-thienyl)benzene, 2,5-diamino-1-(4-(methoxy-ethyl)aminomethyl-3-thienyl)benzene, 2,5-diamino-1-(4-(3,4-dimethoxyphenyl)aminomethyl-3-thienyl)benzene, 2,5-diamino-1-(4-(4-trifluormethylbenzyl)aminomethyl-3-thienyl)-benzene, 2,5-diamino-1-(4-(3-methoxyphenyl)aminomethyl-3-thienyl)-benzene, 2,5-diamino-1-(4-(O,N-dimethylhydroxylaminomethyl-3-thienyl)benzene, 2,5-diamino-1-(4-(2,4-dimethoxy-5-chloro-phenyl)aminomethyl-3-thienyl)benzene, 2,5-diamino-1-(4-(4-phenoxyphenyl)aminomethyl-3-thienyl)benzene, 2,5-diamino-1-(4-(2-diphenyl)aminomethyl-3-thienyl)benzene, 2,5-diamino-1-(4-(3,4-dimethoxybenzyl)aminomethyl-3-thienyl)benzene, 2,5-diamino-1-(4-(4-methoxyphenyl)aminomethyl-3-thienyl)-benzene, 2,5-diamino-1-(4-(4-hydroxybutyl)aminomethyl-3-thienyl)benzene, 2,5-diamino-1-(4-(2-methoxy-3-fluorophenyl)aminomethyl-3-thienyl)benzene, 2,5-diamino-1-(4-(4-(1-phenylethyl)aminomethyl-3-thienyl)benzene, 2,5-diamino-1-(4-(2-furyl)aminomethyl-3-thienyl)benzene, 2,5-diamino-1-(4-(2-pyridyl)aminomethyl-3-thienyl)benzene, 2,5-diamino-1-(4-morpholinomethyl-3-thienyl)benzene, 2,5-diamino-1-(4-4-benzyl-pyperazinomethyl-3-thienyl)benzene, 2,5-diamino-1-(4-(3-carboxamidphenyl)aminomethyl-3-thienyl)benzene, 2,5-diamino-1-(4-(N-methyl-N-phenyl)aminomethyl-3-thienyl)benzene, 2,5-diamino-1-(4-diethylaminomethyl-3-thienyl)benzene, 2,5-diamino-1-(4-(pyridin-4-yl-methyl)aminomethyl-3-thienyl)benzene, 2,5-diamino-1-(4-(3,5 -dimethoxybenzyl)-aminomethyl-3-thienyl)benzene, 2,5-diamino-1 -(4-(4-morpholinophenyl)aminomethyl-3-thienyl)benzene, 2,5-diamino-1-(4-(1-(2-hydroxyethyl)))propylaminomethyl-3-thienyl)benzene, 2,5-diamino-1-(4-cyclopropylaminomethyl-3-thienyl)benzene, N-(2-{[4-(2,5-diaminophenyl)-thiophene-2-yl-methyl]-amino}ethyl)acetamide, 2,5-diamino-1-(4-cyclo-hexylaminomethyl-3-thienyl)benzene, 2,5-diamino-1-(4-propylamino-methyl-3-thienyl)benzene, 2,5-diamino-1-(4-(o-tolyl)-aminomethyl-3-thienyl)benzene, 2,5-diamino-1-(4-(N-methyl-N-cyclohexyl)aminomethyl-3-thienyl)benzene, 2,5-diamino-1-(4-(2,6-dimethyl-morpholino)methyl-3-thienyl)benzene, 2,5-diamino-1-(4-(3,5-dimethyl-piper-idino)methyl-3-thienyl)-benzene, 2,5-diamino-1-(4-(3-(1-hydroxyethyl)phenyl)aminomethyl-3-thienyl)benzene, 2,5-diamino-1-(4-(3,4-dimethylphenyl)aminomethyl-3-thienyl)benzene, 2,5-diamino-1-(4-(3-methyl-mercaptophenyl)aminomethyl-3-thienyl)-benzene, 2,5-diamino-1-(4-(4-diphenyl)-aminomethyl-3-thienyl)benzene, 2,5-diamino-1-(4-(4-iso-propylphenyl)aminomethyl-3-thienyl)benzene, 2,5-diamino-1-(4-pentylaminomethyl-3-thienyl)benzene, 2,5-diamino-1-(4-(dibutyl)aminomethyl-3-thienyl)benzene, 2,5-diamino-1-(4-isopropylaminomethyl-3-thienyl)benzene, 2,5-diamino-1-(4-(N-cyclopropylmethyl-N-propyl)aminomethyl-3-thienyl)benzene, 2,5-diamino-1-(4-(4-hydroxy)piperidinomethyl-3-thienyl)benzene, 2,5-diamino-1-(4-(fluorenyl)-aminomethyl-3-thienyl)benzene, 2,5-diamino-1-(4-(4-dimethylaminophenyl)aminomethyl-3-thienyl)benzene, 2,5-diamino-1-(4-(3,5-dimethylphenyl)aminomethyl- 3-thienyl)benzene, 2,5-diamino-1 -(4-(4-methoxybenzyl)aminomethyl-3-thienyl)benzene, 2,5-diamino-1-(4-(indanyl)aminomethyl-3-thienyl)-benzene, 2,5-diamino-1-(4-(3-fluorobenzyl)aminomethyl-3-thienyl)benzene, 2,5-diamino-1-(4-(benzyl)amino-methyl-3-thienyl)benzene, 2,5-diamino-1-(4-(4-methyl-piperazino)aminomethyl-3-thienyl)benzene, 2,5-diamino-1-(4-(4-tert-butylphenyl)aminomethyl-3-thienyl)benzene, 2,5-diamino-1-(4-(2-chlorobenzyl)aminomethyl-3-thienyl)benzene, 2,5-diamino-1-(4-(naphth-1-yl-methyl)aminomethyl-3-thienyl)-benzene, 2,5-diamino-1-(4-(phenyl)aminomethyl-3-thienyl)

benzene, 2,5-diamino-1-(4-(4-chlorophenyl)-aminomethyl-3-thienyl)benzene, 4-{[4-(2,5-diamino-phenyl)thiophen-2-yl-methyl]amino}benzoic acid and 2,5-diamino-1-(3-thienyl)benzene.

The compound 2,5-diamino-1-(3-thienyl)benzene is particularly preferred.

The compounds of formula (I) can be used both as free bases and also in the form of their physiologically compatible salts with inorganic or organic acids, for example hydrochloric acid, sulfuric acid, phosphoric acid, acetic acid, propionic acid, lactic acid or citric acid.

The diaminobenzene derivative compounds of formula (I) according to the invention can be made by known synthesis methods. The synthesis of the compounds according to the invention can, for example, be performed as follows: a) by a tetrakis(triphenylphosphine)palladium(0) catalyzed coupling of a substituted benzene of formula (II):

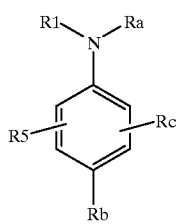

(II)

with a heterocompound of the formula (III):

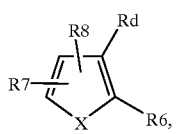

(III)

in which Ra represents a protective group, such as described in the chapter "Protective Groups" in Organic Synthesis, Chapter 7, Wiley Interscience, 1991, Rb represents $NR1Ra$ or $NO_2$, Rc represents halogen and Rd represents $B(OH)_2$ or Rc represents $B(OH)_2$ and Rd represents halogen, and X, R1, R5, R6, R7 and R8 have the same significance as in formula (I); and then by subsequent splitting off of the protective group or by subsequent splitting off of the protective group and reduction of the nitro group;

or (b) by a tetrakis(triphenylphosphine)palladium(0) catalyzed coupling of a substituted benzene of formula (IV):

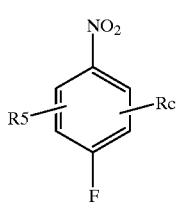

(IV)

with a heteroaryl compound of the formula (III):

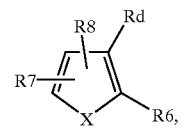

(III)

in which Rc represents halogen and Rd represents $B(OH)_2$ or Rc represents $B(OH)_2$ and Rd represents halogen; and X, R5, R6, R7 and R8 have the same significance as in formula (I), with subsequent substitution of the benzene of formula (V) so obtained

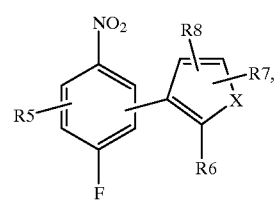

(V)

with an amine of formula HNR1R2, wherein R1,R2 have the same significance as in formula (I), and with reduction of the nitro group.

The diaminobenzene derivative compounds of formula (I) are soluble in water and provide colors with higher color intensity and outstanding color fastness, especially light fastness, fastness to washing and fastness to rubbing. Furthermore the compounds of formula (I) have an outstanding storage stability, especially as ingredients of the above-mentioned dye compositions.

The subject matter of the invention also includes compositions for oxidative dyeing of keratin fibers, for example hair, fur, feathers or wool, especially human hair, based on a developer-coupler combination which includes a diaminobenzene derivative compound of the above formula (I) as developer substance.

The diaminobenzene derivative compound of formula (I) is contained in the dye composition according to the invention in an amount of from about 0.005 to 20 percent by weight, preferably however from about 0.01 to 5.0 percent by weight, and especially preferably from 0.1 to 2.5 percent by weight.

The coupler substance preferably can be 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[(di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis(2- hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methyphenol, 5-amino-4-ethoxy-2-methylphenol, 3-amino-2,4-dicholorophenol, 5-amino-2,4-dichlorophenol, 3-amino-2-methylphenol, 3-amino-2-chloro-6-methylphenol, 3-aminophenol, 2-{(3-hydroxyphenyl)amino]-acetamide, 5-[(2-hydroxyethyl)amino]-2-methylphenol, 3-[(2-hydroxyethyl)aminophenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydoxynaphthalene, 2,7-dihydoxynaphthalene, 2-methyl-1-naphthaol acetate, 1,3-dihydoxybenzene, 1-chloro- 2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxy-phenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolindione.

Although the advantageous properties of the above-described diaminobenzene derivative compounds of formula (I) can obviously be obtained when the diaminobenzene derivative compounds of formula (I) are used alone, it is understandably also possible to use the diaminobenzene derivative compounds of formula (I) together with known developer substances, such as 1,4-diaminobenzene, 2,5-diaminotoluene, 2,5-diaminophenylethyl alcohol, 4-aminophenol and its derivatives, especially 4-amino-3-methylphenol, 4,5-diamino-1-(2-hydroxyethyl)pyrazole or tetraaminopyrimidines.

The coupler and developer substances can be contained in the dye compositions according to the invention individually, or in mixtures with each other. The total amount of coupler substances and developer substances in the dye composition according to the invention (relative to the total amount of the dye composition) is from about 0.005 to 20 percent by weight respectively, preferably from about 0.01 to 5.0 percent by weight and especially preferably from 0.1 to 2.5 percent by weight.

The total amount of the combination of developer and coupler substances in the dye composition described here is preferably from about 0.01 to 20 percent by weight, especially preferably from about 0.02 to 10 percent by weight, and most preferably from 0.2 to 6.0 percent by weight. The developer and coupler substances are used generally in equimolar amounts, however it is not disadvantageous when the developer substances are present in a certain excess or deficiency.

The dye compositions according to the invention can also contain certain other dye ingredients, for example 6-amino-2-methylphenol and 2-amino-5-methylphenol, as well as conventional direct-dyeing dye compounds, such as triphenylmethane dye compounds, such as 4-[(4'-aminophenyl)-(4'-imino-2",5"-cyclohexadien-1"-yliden)-methyl]-2-methylaminobenzene monohydrochloride (C.I. 42 510) and 4-[(4'-amino-3'-methylphenyl)-(4"-imino-2", 5"-cyclohexadien-1"-yliden)methyl]-2-methylaminobenzene monohydrochloride (C.I. 42 520); aromatic nitro dye compounds, such as 4-(2"-hydroxyethyl)amino-nitrotoluene, 2-amino-4,6-dinitrophenol, 2-amino-5-(2'-hydroxyethyl)aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-[(2'-ureidoethyl)amino-4-nitrobenzene; azo dye compounds, such as 6-[(4'-aminophenyl)azo]-5-hydroxy-napththalen-1-sulfonic acid sodium salt (C.I. 14 805) and dispersion dye compounds, such as 1,4-diaminoanthraquinone and 1,4,5,8 tetraaminoanthraquinone. These dye compounds can be contained in the dye composition of the invention in an amount of from about 0.1 to 4.0 percent by weight.

Understandably the coupler substances and the developer substances as well as the other dye compounds, in so far as they are bases, can also be used in the form of their physiologically compatible salts with organic or inorganic acids, such as hydrochloric acid or sulfuric acid, or, in so art as they have aromatic OH groups, in the form of their salts with bases, such as alkali phenolates.

Moreover cosmetic additive ingredients, which are commonly used in compositions for dyeing hair, can be used in the dye compositions according to the invention, for example antioxidants, such as ascorbic acid, thioglycolic acid or sodium sulfite, and perfume oils, complex formers, wetting agents, emulsifiers, thickeners and care materials. The form of the dye compositions according to the invention can be, for example, a solution, especially an aqueous or aqueous-alcoholic solution. However the form that is particularly preferred is a cream, gel or an emulsion. Its composition is a mixture of the dye ingredients with the conventional cosmetic additive ingredients suitable for the particular preparation.

Conventional cosmetic additive ingredients in solutions, creams, emulsion or gels include, for example, solvents, such as water, lower aliphatic alcohols, such as ethanol, propanol or isopropanol, glycerol or glycols, such as 1,2-propylene glycol, wetting agents or emulsifiers from the classes of anionic, cationic, amphoteric or nonionic surfactant compounds, such as fatty alcohol sulfates, ethoxylated fatty alcohol sulfates, alkylsulfonates, alkylbenzenesulfonates, alkyltrimethylammonium salts, aklylbetaines, ethoxylated fatty alcohols, ethoxylated nonylphenols, fatty acid alkanol amides and ethoxylated fatty acid esters; thickeners, such as higher fatty alcohols, starches, cellulose derivatives, petrolatum, paraffin oil and fatty acids, as well as care materials, such as cationic resins, lanolin derivatives, cholesterol, pantothenic acids and betaine. The above-mentioned conventional cosmetic ingredients are used in amounts suitable for their purposes. For example the wetting agents and emulsifiers are used in concentrations of from about 0.5 to 30 15 percent by weight, the thickeners are used in an amount of from about 0.1 to 25 percent by weight and the care materials are used in concentrations of from about 0.1 to 5.0 percent by weight.

The dye compositions according to the invention can be weakly acidic, neutral or alkaline according to their composition. The compositions especially have pH values of from 6.8 to 11.5. Their pH can be adjusted in the basic range with ammonia. Also organic amines can be used for this purpose, including monoethanolamine and triethanolamine, or also inorganic bases, such as sodium hydroxide and potassium hydroxide. Inorganic or organic acids can be used for adjusting the pH in the acid range, for example phosphoric acid, acetic acid, citric acid or tartaric acid.

In order to use the oxidation hair dye composition for dyeing hair one mixes the above-described dye compositions according to the invention with an oxidizing agent immediately prior to use and applies a sufficient amount of the mixture to the hair, according to the hair abundance, generally from about 60 to 200 grams.

Principally hydrogen peroxide, or its addition compounds with urea, melamine, sodium borate or sodium carbonate, can be used in the form of a 3 to 12 percent, preferably 6 percent, aqueous solution as the oxidizing agent for developing the hair dye, Air oxygen can also be used as the oxidizing agent. If a 6 percent hydrogen peroxide solution is used as oxidizing agent, the weight ratio of hair dye composition and oxidizing agent is 5:1 to 1:2, but preferably 1:1. Larger amounts of oxidizing agent are used above all with larger dye concentrations in the hair dye composition, or when at the same time a strong bleaching of the hair is desired. The mixture of the oxidizing agent and the dye composition of the invention is allowed to act on the hair for about 10 to 45 minutes, preferably 30 minutes, at 15 to 65 degrees Celsius, the hair is rinsed with water and dried. If necessary it is washed with a shampoo and eventually after-rinsed with a weak organic acid, such as citric acid or tartaric acid.

Subsequently the hair is dried.

The hair dye composition according to the invention with a content of diaminobenzene derivative compounds of formula (I) as developer substances permits hair dyeing with outstanding color fastness, especially light fastness, fastness to washing and fastness to rubbing. The dye composition according to the invention provides a broad palette of different color shades, which extend from blond to brown, purple, violet to blue and black shades, according to the type and composition of the dye compounds in it. Particularly the color shades produced have outstanding color intensity. The very good dyeing properties of the compositions according to the invention include the production of good color coverage and dyeing of gray, chemically not-previously damaged hair without problems.

The following examples should serve to illustrate the invention, but details present in these examples should not be considered as further limiting the following appended claims, unless they are explicitly included in the following appended claims.

EXAMPLES

Example 1

Synthesis of 2,5-diamino-1-(3-thienyl)benzenes (General Synthetic Recipe)

A. Synthesis of 2,5-tert-butyloxycarbonylaminobromobenzene 15.65 g (0.07 mol)bromo-p-phenylenediamine hydrochloride and 32.7 g (0.15 mol)di-tert.-butyl-dicarbonate are dissolved in a mixture of 250 ml 2N sodium hydroxide and 250 ml trifluorotoluene and heated at 45° C. This reaction mixture is stirred for 3 days. Then 30 g (0.14 mol) di-tert.butyl dicarbonate is added stepwise. Subseqeuntly the organic layer is separated and the aqueous phase is extracted twice with 100 ml dichloromethane. The combined extracts are evaporated to dryness and the residue is taken up in 200 ml of hexane. The precipitate is filtered and washed with 50 ml hexane. 18.6 g (82% of theoretical) of 2,5-tert.-butyloxycarbonylaminobromobenzene is obtained with a melting point of 130° C.

B. Synthesis of 2,5-diamino-1-(3-thienyl)benzenes 3.3 g (0.01 mol) 2,5-tert.-butyloxycarbonylaminobromobenzene from step A and 0.013 mol of the corresponding boric acid are dissolved in 70 ml of 1,2-dimethyoxyethane under argon. Subsequently 0.5 g tetrakis(triphenylphosphine)palladium (0.0005 mol) and 13 ml 2N potassium carbonate are added and the resulting reaction mixture is heated to 80° C. After termination of the reaction, the reaction mixture is poured into 100 ml acetic acid ethyl ester, the organic phase is extracted with dilute sodium hydroxide and then dried with magnesium sulfate. The solvent is distilled off in a rotary evaporator and the residue is purified on silica gel with petroleum ether/acetic acid ethyl ester (9:1). The product obtained in this way is heated to 50° C. in ethanol. Then 15 ml of a 2.9 molar ethanolic hydrochloric acid solution is added dropwise to make the hydrochloride salt. The precipitate is filtered, washed twice with 10 ml ethanol and then dried.

2,5-diamino-1-(3-thienyl)benzene dihydrochloride

Boric acid used: thiophen-3-boric acid

Yield: 2.0 g (75% of theoretical)

Melting Point: 245° C. (colorless crystals)

CHN Analysis:

| $C_{10}H_{12}N_2Cl_2S$ | % C | % H | % N |
| --- | --- | --- | --- |
| Calculated | 45.64 | 4.60 | 10.64 |
| Found | 45.55 | 4.66 | 10.64 |

C. Synthesis of N,N'-bis-(tert.-butoxycarbonyl)-2,5-diamino-1-phenylboric acid.

N,N'-bis-(tert.-butoxycarbonyl)-2,5-diamino-1-phenylboric acid is made by reaction of N,N'-bis-(tert.-butoxycarbonyl)-2,5-diamino-1-bromobenzene with tert-butyl lithium and trimethylborate. The experimental prescription of this synthetic method is described in the article by J. M. Tour and J. J. Lamba in J. Am. Chem. Soc. 1994, 116, p. 11723.

D. Synthesis of 2,5-Diamino-1-(3-thienyl)benzene and 2,5-diamino-1-(3-furyl)benzene 0.035 g (0.0001 mol) 2,5-tert.-butyloxycarbonylamino-1-phenyl-boric acid from step C and 0.00015 mol of the corresponding bromo derivatives are dissolved in 10 ml 1,2-diimethoxyethane under argon. Then 0.005 g tetrakis-(triphenylphophine)-palladium (0.000005 mol) and 0.13 ml of 2 N potassium carbonate solution are added dropwise and the reaction mixture is heated to 80° C. After halting the reaction the reaction mixture is poured into 10 ml of acetic acid ethyl ester, the organic phase is extracted with dilute sodium hydroxide and then dried with magnesium sulfate. The solvent is distilled off with a rotary evaporator and the residue is purified on silica gel with petroleum ether/acetic acid ethyl ester (9:1). The product so obtained is heated to 50° C. in ethanol. Finally 1.5 ml of a 2.9 molar ethanolic hydrochloric acid solution is added dropwise to make the hydrochloride. The precipitate is filtered off, washed twice with 1 ml ethanol and then dried.

a. 2,5-diamino-1-(5-methyl-3-thienyl)benzene dihydrochloride

Bromo derivative used: 3-bromo-4-methylthiophene

Yield: 0.025 g (90% theoretical)

Mass spectra $M^+$ 205(100)

b. 2,5-diamino-1-(2-chloro-3-thienyl)benzene dihydrochloride

Bromo derivative used: 3-bromo-2-chlorothiophene

Yield: 0.025 g (84% theoretical)

Mass spectra $M^+$ 225(100)

c. 2,5-diamino-1-(4-(4-nitropropenyl)-3-thienyl)benzene dihydrochloride

Bromo derivative used: 3-bromo-5-(2-nitropropenyl)thiophene
Yield: 0.025 g (70% theoretical)
Mass spectra MH$^+$ 276(100)

d. 2,5-diamino-1-(3-furyl)benzene dihydrochloride
Bromo derivative used: 3-bromofuran
Yield: 0.025 g (90% theoretical)
Mass spectra MH$^+$ 175(100)

e. 2,5-diamino-1-(4-formyl-3-thienyl)benzene dihydrochloride
Bromo derivative used: 3-bromo-5-formylthiophene
Yield: 0.025 g (71% theoretical)
Mass spectra MH$^+$ 219(100)

E. Synthesis of 2,5-Diamino-1-(4-aminomethyl-3-thienyl)benzene 0.030 g (0.0001 mol) 2,5-tert.-butyloxycarbonylamino-1-(4-(4-formyl-3-thienyl)benzene from step D.e and 0.00015 mol of the corresponding amine are dissolved in methanol and reduced with NaBH$_4$. After halting the reaction the reaction mixture is poured into 10 ml acetic acid ethyl ester, the organic phase is extracted with dilute sodium hydroxide and then dried with magnesium sulfate. The solvent is distilled off in a rotary evaporator and the residue is purified on silica gel with petroleum ether/acetic acid ethyl ester (9:1). The product obtained in this way is heated to 50° C. in 4 ml ethanol. Then 1.5 ml of a 2.9 molar ethanolic hydrochloric acid solution is added dropwise to make the hydrochloride salt. The precipitate is filtered, washed twice with 10 ml ethanol and then dried.

a. 2,5-diamino-1-(4-(2-hydroxyethyl)aminomethyl-3-thienyl)benzene dihydrochloride
Amine used: ethanolamine
Yield: 0.025 g (67% theoretical)
Mass spectra M$^+$ 264(100)

b. 2,5-diamino-1-(4-pyrrolidinomethyl -3-thienyl)benzene dihydrochloride
Amine used: pyrrolidine
Yield: 0.025 g (65% theoretical)
Mass spectra MH$^+$ 274(100)

c. 2,5-diamino-1-(4-(dimethylaminoethyl)aminomethyl-3-thienyl)benzene dihydrochloride
Amine used: dimethylaminoethylamine
Yield: 0.025 g (57% theoretical)
Mass spectra M$^+$ 291(100)

d. 2,5-diamino-1-(4-(2-methoxy-5-chlorophenyl)aminomethyl-3-thienyl)benzene dihydrochloride
Amine used: 2-methoxy-5-chloroaniline
Yield: 0.025 g (53% theoretical)
Mass spectra MH$^+$ 360(100)

e. 2,5-diamino-1-(4-(3-ethoxypropyl)aminomethyl-3-thienyl)benzene dihydrochloride
Amine used: 3-ethoxypropylamine
Yield: 0.025 g (60% theoretical)
Mass spectra MH$^+$ 306(100)

f. 2,5-diamino-1-(4-(methoxyethyl)aminomethyl-3-thienyl)benzene dihydrochloride
Amine used: methoxyethylamine
Yield: 0.025 g (64% theoretical)
Mass spectra MH$^+$ 278(100)

g. 2,5-diamino-1-(4-(3,4-dimethoxyphenyl)aminomethyl-3-thienyl)benzene dihydrochloride
Amine used: 3,4-dimethoxyaniline
Yield: 0.025 g (54% theoretical)
Mass spectra MH$^+$ 356(100)

h. 2,5-diamino-1-(4-(4-trifluoromethylbenzyl)aminomethyl-3-thienyl)benzene dihydrochloride
Amine used: 4-trifluoromethylbenzylamine
Yield: 0.025 g (54% theoretical)
Mass spectra MH$^+$ 378(100)

i. 2,5-diamino-1-(4-(3-methoxyphenyl)aminomethyl-3-thienyl)benzene dihydrochloride
Amine used: 2-methoxyaniline
Yield: 0.025 g (57% theoretical)
Mass spectra MH$^+$ 326(100)

j. 2,5-diamino-1-(4-(O,N-dimethylhydroxy)aminomethyl-3-thienyl)benzene dihydrochloride
Amine used: 0,N-dimethylhydroxylamine
Yield: 0.025 g (67% theoretical)
Mass spectra MH$^+$ 264(100)

k. 2,5-diamino-1-(4-(2,4-dimethoxy-5-chlorophenyl)aminomethyl-3-thienyl)benzene dihydrochloride
Amine used: 2,4-dimethoxy-5-chloroaniline
Yield: 0.025 g (50% theoretical)
Mass spectra MH$^+$ 390(100)

l. 2,5-diamino-1-(4-(4-phenoxyphenyl)aminomethyl-3-thienyl)benzene dihydrochloride
Amine used: 4-phenoxyaniline
Yield: 0.025 g (50% theoretical)
Mass spectra MH$^+$ 388(100)

m. 2,5-diamino-1-(4-(2-diphenyl)aminomethyl-3-thienyl)benzene dihydrochloride
Amine used: 2-diphenylamine
Yield: 0.025 g (52% theoretical)
Mass spectra MH$^+$ 372(100)

n. 2,5-diamino-1-(4-(3,4-dimethoxybenzyl)aminomethyl-3-thienyl)benzene dihydrochloride
Amine used: 3,4-dimethoxybenzylamine
Yield: 0.025 g (52% theoretical)
Mass spectra MH$^+$ 370(100)

o. 2,5-diamino-1-(4-(4-methoxyphenyl)aminomethyl-3-thienyl)benzene dihydrochloride
Amine used: 4-methoxyaniline
Yield: 0.025 g (50% theoretical)
Mass spectra MH$^+$ 326(100)

p. 2,5-diamino-1-(4-(4-hydroxybutyl)aminomethyl-3-thienyl)benzene dihydrochloride
Amine used: 4-hydroxybutylamine
Yield: 0.025 g (62% theoretical)
Mass spectra MH$^+$ 292(100)

q. 2,5-diamino-1-(4-(2-methoxy-3-fluorophenyl)aminomethyl-3-thienyl)benzene dihydrochloride
Amine used: 4-methoxy-3-fluoroaniline
Yield: 0.025 g (55% theoretical)
Mass spectra MH$^+$ 344(100)

r. 2,5-diamino-1-(4-(4-(1-phenylethyl)aminomethyl-3-thienyl)benzene dihydrochloride
Amine used: 1-phenylethylamine
Yield: 0.025 g (58% theoretical)
Mass spectra MH$^+$ 324(100)

s. 2,5-diamino-1-(4-(2-furyl)aminomethyl-3- thienyl)benzene dihydrochloride
Amine used: 2-furylamine
Yield: 0.025 g (61% theoretical)
Mass spectra MH$^+$ 300(100)

t. 2,5-diamino-1-(4-(2-pyridyl)aminomethyl-3-thienyl)benzene dihydrochloride
Amine used: 2-aminopyridine
Yield: 0.025 g (56% theoretical)
Mass spectra MH$^+$ 297(100)

u. 2,5-diamino-1-(4-morpholinomethyl-3-thienyl)benzene dihydrochloride
Amine used: morpholine
Yield: 0.025 g (63% theoretical)
Mass spectra MH$^+$ 290(100)

v. 2,5-diamino-1-(4-benzylpyperazinomethyl-3-thienyl)benzene dihydrochloride
  Amine used: 4-benzylpyperazine
  Yield: 0.025 g (47% theoretical)
  Mass spectra MH+ 379(100)
w. 2,5-diamino-1-(4-(3-carboxamidphenyl)aminomethyl-3-thienyl)benzene dihydrochloride
  Amine used: 3-aminobenzamide
  Yield: 0.025 g (56% theoretical)
  Mass spectra MH+ 339(100)
x. 2,5-diamino-1-(4-(N-methyl-N-phenyl)aminomethyl-3-thienyl)benzene dihydrochloride
  Amine used: N-methyl-N-phenylamine
  Yield: 0.025 g (59% theoretical)
  Mass spectra MH+ 310(100)
v. 2,5-diamino-1-(4-diethylaminomethyl-3-thienyl)benzene dihydrochloride
  Amine used: diethylamine
  Yield: 0.025 g (65% theoretical)
  Mass spectra MH+ 276(100)
z. 2,5-diamino-1-(4-(pyridin-4-yl-methyl)aminomethyl-3-thienyl)benzene dihydrochloride
  Amine used: 4-aminomethylpyridine
  Yield: 0.025 g (55% theoretical)
  Mass spectra MH+ 311(100)
a'. 2,5-diamino-1-(4-(3,5-dimethoxybenzyl)aminomethyl-3-thienyl)benzene dihydrochloride
  Amine used: 3,5-dimethoxybenzylamine
  Yield: 0.025 g (52% theoretical)
  Mass spectra MH+ 370(100)
b'. 2,5-diamino-1-(4-(4-morpholinophenyl)aminomethyl-3-thienyl)benzene dihydrochloride
  Amine used: 4-morpholinoaniline
  Yield: 0.025 g (47% theoretical)
  Mass spectra MH+ 381(100)
c'. 2,5-diamino-1-(4-(1-(2-hydroxyethyl)propylaminomethyl-3-thienyl)benzene dihydrochloride
  Amine used: 1-(2-hydroxyethyl)propylamine
  Yield: 0.025 g (62% theoretical)
  Mass spectra MH+ 292(100)
d'. 2,5-diamino-1-(4-cyclopropylaminomethyl-3-thienyl)benzene dihydrochloride
  Amine used: cyclopropylamine
  Yield: 0.025 g (68% theoretical)
  Mass spectra MH+ 260(100)
e'. N-(2-{[4-(2,5-diaminophenyl)thiopen-2-yl-methyl]amino}ethyl)acetamide dihydrochloride
  Amine used: 2-aminoethylacetamide
  Yield: 0.025 g (60% theoretical)
  Mass spectra MH+ 305(100)
f'. 2,5-diamino-1-(4-cyclohexylaminomethyl-3-thienyl)benzene dihydrochloride
  Amine used: cyclohexylamine
  Yield: 0.025 g (60% theoretical)
  Mass spectra MH+ 302(100)
g'. 2,5-diamino-1-(4-propylaminomethyl-3-thienyl)benzene dihydrochloride
  Amine used: propylamine
  Yield: 0.025 g (67% theoretical)
  Mass spectra MH+ 262(100)
h'. 2,5-diamino-1-(4-(o-tolyl)aminomethyl-3-thienyl)benzene dihydrochloride
  Amine used: 2-methylaniline
  Yield: 0.025 g (59% theoretical)
  Mass spectra MH+ 310(100)
i'. 2,5-diamino-1-(4-(N-methyl-N-cyclohexyl)aminomethyl-3-thienyl)benzene dihydrochloride
  Amine used: N-methyl-N-cyclohexylamine
  Yield: 0.025 g (57% theoretical)
  Mass spectra MH+ 316(100)
j'. 2,5-diamino-1-(4-(2,6-dimethylmorpholino)methyl-3-thienyl)benzene dihydrochloride
  Amine used: 2,6-dimethylmorpholine
  Yield: 0.025 g (58% theoretical)
  Mass spectra MH+ 318(100)
k'. 2,5-diamino-1-(4-(3,5-dimethylpiperidino)methyl-3-thienyl)benzene dihydrochloride
  Amine used: 3,5-dimethylpiperidine
  Yield: 0.025 g (59% theoretical)
  Mass spectra MH+ 340(100)
l'. 2,5-diamino-1-(4-(3-(1-hydroxyethyl)phenyl)aminomethyl-3-thienyl)benzene dihydrochloride
  Amine used: 3-(1-hydroxyethyl)aniline
  Yield: 0.025 g (55% theoretical)
  Mass spectra MH+ 340(100)
m'. 2,5-diamino-1-(4-(3,4-dimethylphenyl)aminomethyl-3-thienyl)benzene dihydrochloride
  Amine used: 3,4-dimethylaniline
  Yield: 0.025 g (58% theoretical)
  Mass spectra MH+ 324(100)
n'. 2,5-diamino-1-(4-(3-methylmercaptophenyl)aminomethyl-3-thienyl)benzene dihydrochloride
  Amine used: 3-methylmercaptoaniline
  Yield: 0.025 g (55% theoretical)
  Mass spectra MH+ 342(100)
o'. 2,5-diamino-1-(4-(4-diphenyl)aminomethyl-3-thienyl)benzene dihydrochloride
  Amine used: 4-aminobiphenyl
  Yield: 0.025 g (52% theoretical)
  Mass spectra MH+ 372(100)
p'. 2,5-diamino-1-(4-(4-isopropylphenyl)aminomethyl-3-thienyl)benzene dihydrochloride
  Amine used: 4-isopropylaniline
  Yield: 0.025 g (56% theoretical)
  Mass spectra MH+ 338(100)
q'. 2,5-diamino-1-(4-pentylaminomethyl-3-thienyl)benzene dihydrochloride
  Amine used: pentylamine
  Yield: 0.025 g (63% theoretical)
  Mass spectra MH+ 290(100)
r'. 2,5-diamino-1-(4-(dibutyl)aminomethyl-3-thienyl)benzene dihydrochloride
  Amine used: dibutylamine
  Yield: 0.025 g (57% theoretical)
  Mass spectra MH+ 332(100)
s'. 2,5-diamino-1-(4-isopropylaminomethyl-3- thienyl)benzene dihydrochloride
  Amine used: isopropylamine
  Yield: 0.025 g (67% theoretical)
  Mass spectra MH+ 262(100)
t'. 2,5-diamino-1-(4-(N-cyclopropylmethyl-N-propyl)aminomethyl-3-thienyl)benzene dihydrochloride
  Amine used: N-cyclopropylmethylpropylamine
  Yield: 0.025 g (59% theoretical)
  Mass spectra MH+ 316(100)
u'. 2,5-diamino-1-(4-(4-hydroxy)piperidinomethyl-3-thienyl)benzene dihydrochloride
  Amine used: 4-hydroxypiperidine
  Yield: 0.025 g (60% theoretical)
  Mass spectra MH+ 304(100)
v'. 2,5-diamino-1-(4-(fluorenyl)aminomethyl-3-thienyl)benzene dihydrochloride Amine used: 2-aminofluorene
Yield: 0.025 g (51% theoretical)
Mass spectra MH+ 384(100)

w'. 2,5-diamino-1-(4-(4-dimethylaminophenyl) aminomethyl-3-thienyl)benzene dihydrochloride
Amine used: 4-dimethylaminoaniline
Yield: 0.025 g (52% theoretical)
Mass spectra MH+ 339(100)

x'. 2,5-diamino-1-(4-(3,5-dimethylphenyl)aminomethyl-3-thienyl)benzene dihydrochloride
Amine used: 3,5-dimethylaniline
Yield: 0.025 g (58% theoretical)
Mass spectra MH+ 324(100)

y'. 2,5-diamino-1-(4-(4-methoxybenzyl)aminomethyl-3-thienyl)benzene dihydrochloride
Amine used: 4-methoxybenzylamine
Yield: 0.025 g (55% theoretical)
Mass spectra MH+ 340(100)

z'. 2,5-diamino-1-(4-(indanyl)aminomethyl-3-thienyl)benzene dihydrochloride
Amine used: 1-aminoindane
Yield: 0.025 g (56% theoretical)
Mass spectra MH+ 336(100)

a". 2,5-diamino-1-(4-(3-fluorobenzyl)aminomethyl-3-thienyl)-benzene dihydrochloride
Amine used: 3-fluorobenzylamine
Yield: 0.025 g (57% theoretical)
Mass spectra MH+ 328(100)

b". 2,5-diamino-1-(4-(benzyl)aminomethyl-3-thienyl)benzene dihydrochloride
Amine used: benzylamine
Yield: 0.025 g (60% theoretical)
Mass spectra MH+ 310(100)

c". 2,5-diamino-1-(4-(4-methylpiperazino)aminomethyl-3-thienyl)benzene dihydrochloride
Amine used: 4-methylpiperarzine
Yield: 0.025 g (56% theoretical)
Mass spectra MH+ 303(100)

d". 2,5-diamino-1-(4-(4-tert.butylphenyl)aminomethyl-3-thienyl)benzene dihydrochloride
Amine used: 4-tert.-butylaniline
Yield: 0.025 g (54% theoretical)
Mass spectra MH+ 352(100)

e". 2,5-diamino-1-(4-(2-chlorobenzyl)aminomethyl-3-thienyl)benzene dihydrochloride
Amine used: 2-chlorobenzylamine
Yield: 0.025 g (55% theoretical)
Mass spectra MH+ 344(100)

f". 2,5-diamino-1-(4-(naphth-1-yl-methyl)aminomethyl-3-thienyl)benzene dihydrochloride
Amine used: 1-aminomethylnaphthalene
Yield: 0.025 g (53% theoretical)
Mass spectra MH+ 360(100)

g". 2,5-diamino-1-(4-(phenyl)aminomethyl-3-thienyl)benzene dihydrochloride
Amine used: aniline
Yield: 0.025 g (62% theoretical)
Mass spectra MH+ 296(100)

h". 2,5-diamino-1-(4-(4-chlorophenyl)aminomethyl-3-thienyl)benzene dihydrochloride
Amine used: 4-chloroaniline
Yield: 0.025 g (57% theoretical)
Mass spectra MH+ 330(100)

i". 4-{[4-(2,5-diaminophenyl)thiophen-2-yl-methyl]amino}-benzoic acid methyl ester dihydrochloride
Amine used: 4-aminobenzoic acid methyl ester
Yield: 0.025 g (54% theoretical)
Mass spectra MH+ 354(100)

Example 2

Synthesis of 2-N-substituted 2-amino-5-amino-1-(3-thienyl)benzenes (General Synthesis)

A. Synthesis of 2-fluoro-5-nitro -1-(3-thienyl)benzene 1.75 g (0.01 mol) 1-chloro-2-fluoro-5-nitrobenzene and 0.013 mol thiophen-3-boric acid are dissolved in 70 ml 1,2-dimethoxyethane under argon. Subsequently 0.5 g tetrakis-(triphenylphosphine)palladium (0.0005 mol) and 13 ml 2N potassium carbonate are added and the resulting reaction mixture is heated to 80° C. After termination of the reaction, the reaction mixture is poured into 100 ml acetic acid ethyl ester, the organic phase is extracted with dilute sodium hydroxide and then dried with magnesium sulfate. The solvent is distilled off in a rotary evaporator and the residue is purified on silica gel with hexane/acetic acid ethyl ester (20:1). 1.24 g (56% of theoretical) of the product 2-fluoro-5-nitro-1-(3-thienyl)benzene were obtained with a melting point of 65° C.

B. Synthesis of 2-N-substituted-2-amino-5-amino-1-(3-thienyl)-Benzenes 0.56 g (0.0025 mol)2-fluoro-5-nitro-1-(3-thienyl)benzene from step A and 5 ml of the corresponding amine are dissolved in ethanol. Subsequently the reaction mixture is heated to 80° C. After halting the reaction the reaction mixture is poured into 50 g of ice, extracted with acetic acid ethyl ester and then dried with magnesium sulfate. The solvent is distilled off in a rotary evaporator and the residue is purified on silica gel with dichloromethane/ethanol (50:1). The product thus obtained is dissolved in 30 ml ethanol and hydrogenated under addition of 100 mg of a palladium-activated carbon catalyst (10%) at 50° C. After up-take of the required amount of hydrogen the product-containing mixture is filtered to remove the catalyst and the solvent is distilled of in a rotary evaporator. Then 5 ml of 2.9 molar ethanolic hydrochloric acid solution is added dropwise to prepare the hydrochloride salt. The precipitate is filtered off, washed twice with 10 ml of ethanol and then dried.

a. 2-dimethylamino-5-amino-1-(3-thienyl)benzene dihydrochloride
Amine used: dimethylamine
Yield: 0.27 g (36% theoretical)
Melting point: 232° C.(decomposes) (colorless crystals)
CHN Analysis:

| $C_{12}H_{16}N_2Cl_2S$ | % C | % H | % N |
| --- | --- | --- | --- |
| Calculated | 49.48 | 5.54 | 9.61 |
| Found: | 48.77 | 5.84 | 9.46 | b. 2-pyrrolidino-5-amino-1-(3-thienyl)benzene dihydrochloride
Amine used: pyrrolidine
Yield: 0.55 g (69% theoretical)
Melting point: 205° C.(decomposes) (colorless crystals)
CHN Analysis

| $C_{14}H_{18}N_2Cl_2S$ | % C | % H | % N |
| --- | --- | --- | --- |
| Calculated: | 52.99 | 5.72 | 8.83 |
| Found: | 52.00 | 5.77 | 8.60 | c. 2-di (2-hydroxyethyl)amino-5-amino-1-(3-thienyl) benzene dihydrochloride
  Amine used: diethanolamine
  Yield: 0.14 g (16% theoretical)
  Melting point: 208° C.(decomposes) (colorless crystals)
CHN Analysis:

| $C_{14}H_{20}N_2OCl_2S$ | C % | % H | % N |
|---|---|---|---|
| Calculated: | 47.86 | 5.74 | 7.97 |
| Found: | 47.33 | 5.74 | 7.90 | d. 2-(2-hydroxyethyl)amino-5-amino-1-(3-thienyl)benzene dihydrochloride
  Amine used: ethanolamine
  Yield: 0.5 g (42% theoretical)
  Melting point: 208° C.(decomposes) (colorless crystals)
CHN Analysis:

| $C_{12}H_{16}N_2OCl_2S$ | C % | % H | % N |
|---|---|---|---|
| Calculated: | 46.91 | 5.25 | 9.12 |
| Found: | 46.45 | 5.43 | 9.13 | e. 2-(2-methoxyethyl)amino-5-amino-1-(3-thienyl)benzene dihydrochloride
  Amine used: 2-methoxyethylamine
  Yield: 0.50 g (42% theoretical)
  Melting point: 208° C.(decomposes) (colorless crystals)
CHN Analysis:

| $C_{13}H_{18}N_2OCl_2S$ | C % | % H | % N |
|---|---|---|---|
| Calculated: | 48.60 | 5.65 | 8.72 |
| Found: | 48.24 | 6.43 | 8.38 | f. 2-(2,3-dihydroxypropyl)amino-5-amino-1-(3-thienyl) benzene dihydrochloride
  Amine used: 2,3-dihydroxypropylamine
  Yield: 0.35 g (30% theoretical)
  Melting point: 208° C.(decomposes) (colorless crystals)
CHN Analysis:

| $C_{13}H_{18}N_2OCl_2S$ | C % | % H | % N |
|---|---|---|---|
| Calculated: | 46.3 | 5.38 | 8.31 |
| Found: | 44.08 | 6.07 | 8.00 |

Example 3

Synthesis of 2,5-diamino-4-methyl-1-(3-thienyl) benzene 1.87 g (0.01 mol) 5-chloro-2-methyl-4-nitroaniline and 0.013 mol thiophene-3-boric acid are dissolved under argon in 70 ml of 1,2-dimethoxyethane. Subsequently 0.5 g tetrakis(tri-phenylphosphine)palladium (0.0005 mol) and 13 ml 2N potassium carbonate solution are added and the reaction mixture heated to 80° C. After termination of the reaction the reaction mixture is poured into 100 ml acetic acid ethyl ester, the organic phase is extracted with dilute sodium hydroxide and then dried with magnesium sulfate. The solvent is distilled off in a rotary evaporator and the residue is purified on silica gel with hexane/acetic acid ethyl ester (20:1). The product obtained is dissolved in 30 ml ethanol and hydrogenated with addition of 100 mg of a palladium-activated carbon catalyst (10%) at 50° C. After up take of the required amount of hydrogen the catalyst is filtered off and the solvent is distilled off in a rotary evaporator. Subsequently 5 ml of a 2.9 molar ethanolic hydrochloric acid solution is added dropwise. The precipitate is filtered off, washed twice with 10 ml ethanol and then dried. The yield is 2.1 g (76% of theoretical).
CHN Analysis:

| $C_{11}H_{14}N_2Cl_2S$ | C % | % H | % N |
|---|---|---|---|
| Calculated: | 47.66 | 5.09 | 10.11 |
| Found: | 48.18 | 5.57 | 9.62 |

Example 4

Synthesis of 2,5-diamino-4-methoxy-1-(3-thienyl) benzene 1.87 g (0.01 mol) 5-chloro-2-methoxy-4-nitroaniline and 0.013 mol thiophene-3-boric acid are dissolved under argon in 70 ml of 1,2-dimethoxyethane. Subsequently 0.5 g tetrakis(tri-phenylphosphine)palladium (0.0005 mol) and 13 ml 2N potassium carbonate solution are added and the reaction mixture heated to 80° C. After termination of the reaction the reaction mixture is poured into 100 ml acetic acid ethyl ester, the organic phase is extracted with dilute sodium hydroxide and then dried with magnesium sulfate. The solvent is distilled off in a rotary evaporator and the residue is purified on silica gel with hexane/acetic acid ethyl ester (20:1). The product obtained is dissolved in 30 ml ethanol and hydrogenated with addition of 100 mg of a palladium-activated carbon catalyst (10%) at 50° C. After up take of the required amount of hydrogen the catalyst is filtered off and the solvent is distilled off in a rotary evaporator. Subsequently 5 ml of a 2.9 molar ethanolic hydrochloric acid solution is added dropwise. The precipitate is filtered off, washed twice with 10 ml ethanol and then dried. The yield is 1.8 g (62% of theoretical).
CHN Analysis:

| $C_{11}H_{14}N_2Cl_2OS$ | C % | % H | % N |
|---|---|---|---|
| Calculated: | 45.06 | 4.81 | 9.55 |
| Found: | 44.98 | 4.86 | 9.50 |

Examples 5 to 12

Hair Dye Compositions

Hair Dye Solutions were prepared having the following composition:

| 0.0125 mol | developer substance according to Table I |
| 0.0125 mol | coupler substance according to Table I |
| 10.0 g | potassium oleate (8 % aqueous solution) |

-continued

| | |
|---|---|
| 10.0 g | ammonia (22 percent aqueous solution) |
| 10.0 g | isopropanol |
| 0.3 g | ascorbic acid |
| to 100.0 g | water |

30 g of the above-described dye solution were mixed immediately prior to use with 30 g of 6 percent hydrogen peroxide solution. Then the mixture was applied to bleached hair. After an acting time of 30 minutes at 40° C., the hair was rinsed with water, washed with a shampoo and dried. The resulting colors for the dyeing hair are summarized in the following Table I.

TABLE I

HAIR DYEING COMPOSITIONS

| EXAMPLE | DEVELOPER OF FORMULA I | COUPLER | COLOR OBTAINED |
|---|---|---|---|
| 5 | 2,5-diamino-1-(3-thienyl)benzene*2HCl | 2-amino-4-(2-hydroxyethyl)aminoanisole sulfate | dark blue |
| 6 | 2,5-diamino-1-(3-thienyl)benzene*2HCl | 1,3-dihydroxybenzene | dark blond |
| 7 | 2,5-diamino-1-(3-thienyl)benzene*2HCl | 1-chloro-2,4-dihydroxybenzene | dark blond |
| 8 | 2-di(2-hydroxyethyl)amino-5-amino-1-(3-thienyl)-benzene*2HCl | 1,3-dihydoxybenzene | blond |
| 9 | 2-pyrrolidino-5-amino-1-(3-thienyl)benzene*2HCl | 2-amino-4-(2-hydroxyethyl)aminoanisole sulfate | blue |
| 10 | 2-(2-hydroxyethyl)amino-5-amino-1-(3-thienyl)-benzene*2HCl | 1,3-dihydoxybenzene | blond |
| 11 | 2-(2-methoxyethyl)amino-5-amino-1-(3-thienyl)-benzene*2HCl | 2-amino-4-(2-hydroxyethyl)aminoanisole sulfate | blue |
| 12 | 2-(2,3-dihydroxypropyl)-amino-5-amino-1-(3-thienyl)-benzene*2HCl | 1,3-dihydoxybenzene | blond |

Examples 13 to 20

Hair Dye Compositions

Hair Dye Solutions were prepared having the following composition:

| | |
|---|---|
| 0.0000125 mol | developer substance of formula (I) according to Table II |
| 0.0000125 mol | coupler substance according to Table II |
| 0.01 g | potassium oleate (8% aqueous solution) |
| 0.01 g | ammonia (22 percent aqueous solution) |
| 0.01 g | ethanol |
| 0.003 g | ascorbic acid |
| to 1.00 g | water |

1 g of the above-described dye solution was mixed immediately prior to use with 1 g of 6 percent hydrogen peroxide solution. Then the mixture was applied to bleached hair. After an acting time of 30 minutes at 40° C., the hair was rinsed with water, washed with a shampoo and dried. The resulting colors for the dyeing hair are summarized in the following Table II.

TABLE II

HAIR DYEING COMPOSITIONS

| EXAMPLE | DEVELOPER OF FORMULA I | COUPLER | COLOR OBTAINED |
|---|---|---|---|
| 13 | 2,5-diamino-1-(5-methyl-3-thienyl)benzene*2HCl | 1,3-diamino-4-(2-hydroxyethoxy)benzyl-aminoanisole sulfate | dark blue |
| 14 | 2,5-diamino-1-(5-methyl-3-thienyl)benzene*2HCl | resorcinol | dark blond |
| 15 | 2,5-diamino-1-(2-chloro-3-thienyl)benzene*2HCl | resorcinol | dark blond |
| 16 | 2,5-diamino-1-(3-furyl)-benzene*2HCl | 1,3-diamino-4-(2-hydroxyethoxy)benzyl-aminoanisole sulfate | dark blue |
| 17 | 2,5-diamino-1-(3-furyl)-benzene*2HCl | resorcinol | dark blond |
| 18 | 2,5-diamino-1-(4-(2-hydroxyethyl)aminomethyl-3-thienyl)benzene*2HCl | 1,3-diamino-4-(2-hydroxyethoxy)benzyl-aminoanisole sulfate | blue |
| 19 | 2,5-diamino-1-(4-propyl)aminomethyl-3-3-thienyl)benzene*2HCl | resorcinol | blond |
| 20 | 2,5-diamino-1-(4-(phenyl)aminomethyl-3-thienyl)benzene*2HCl | resorcinol | blond |

Example 21

Hair Dye Composition

A hair dyeing solution having the following composition was prepared:

| | |
|---|---|
| 0.160 g | 2,5-diamino-1-(3-thienyl)benzene*2HCl |
| 0.160 g | 1,4-diamino-2-(2-hydroxyethyl)benzene sulfate |
| 0.137 g | 1,3-dihydroxybenzene |
| 0.100 g | 1,3-dihydroxy-2-methylbenzene |
| 0.100 g | 2-amino-5-methylphenol |
| 10.000 g | potassium oleate(8 percent aqueous solution) |
| 10.000 g | ammonia (22 percent aqueous solution) |
| 10.000 g | isopropanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a blond color.

Example 22

Hair Dye Composition

A hair dyeing solution having the following composition was prepared:

| | |
|---|---|
| 0.320 g | 2,5-diamino-1-(3-thienyl)benzene*2HCl |
| 0.300 g | 5-amino-2-methylphenol |
| 0.600 g | 4-amino-3-methylphenol |
| 0.600 g | 4-aminophenol |
| 0.100 g | α-naphthol |
| 0.200 g | 2-chloro-6-(ethylamino)-4-nitrophenol |

| | |
|---|---|
| 10.000 g | potassium oleate(8 percent aqueous solution) |
| 10.000 g | ammonia (22 percent aqueous solution) |
| 10.000 g | isopropanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a red color.

Example 23

Hair Dye Composition

A hair dyeing solution having the following composition was prepared:

| | |
|---|---|
| 0.320 g | 2,5-diamino-1-(3-thienyl)benzene*2HCl |
| 0.040 g | 5-amino-2-methylphenol |
| 0.090 g | 2-amino-4-(2'-hydroxyethyl)amino-anisole sulfate |
| 0.030 g | 3-aminophenol |
| 0.030 g | 1,3-dihydroxybenzene |
| 0.040 g | 1,3-dihydroxy-2-methylbenzene |
| 0.100 g | 4-amino-5-methylphenol |
| 0.200 g | 2-amino-3-methylphenol |
| 0.100 g | 2-amino-6-methylphenol hydrochloride |
| 0.010 g | 4-chloro-N-(2-hydroxyethyl)-2-nitroaniline |
| 0.020 g | 2-amino-4,6-dinitrophenol |
| 0.100 g | 2-chloro-6-(ethylamino)-4-nitrophenol |
| 10.000 g | potassium oleate(8 percent aqueous solution) |
| 10.000 g | ammonia (22 percent aqueous solution) |
| 10.000 g | isopropanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 24

Hair Dye Composition

A hair dyeing solution having the following composition was prepared:

| | |
|---|---|
| 0.320 g | 2,5-diamino-1(3-thienyl)benzene*2HCl |
| 0.040 g | 5-amino-2-methylphenol |
| 0.050 g | 1,3-diamino-4-(2-hydroxyethoxy)benzene |
| 0.030 g | 3-aminophenol |
| 0.030 g | 1,3-dihydroxybenzene |
| 0.040 g | 1,3-dihydroxy-2-methylbenzene |
| 0.100 g | 4-amino-5-methylphenol |
| 0.200 g | 2-amino-3-methylphenol |
| 0.100 g | 2-amino-6-methylphenol hydrochloride |
| 0.010 g | 4-chloro-N-(2-hydroxyethyl)-2-nitroaniline |
| 0.020 g | 2-amino-4,6-dinitrophenol |

| | |
|---|---|
| 0.100 g | 2-chloro-6-(ethylamino)-4-nitrophenol |
| 10.000 g | ammonia (22 percent aqueous solution) |
| 10.000 g | isopropanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 25

Hair Dye Composition

A hair dyeing solution having the following composition was prepared:

| | |
|---|---|
| 0.220 g | 2,5-diamino-1-(3-thienyl)benzene*2HCl |
| 0.100 g | 1,4-diamino-2-(2-hydroxyethyl)benzene sulfate |
| 0.020 g | 5-amino-2-methylphenol |
| 0.010 g | 1,3-diamino-4-(2-hydroxyethoxy)benzene sulfate |
| 0.004 g | 2-amino-4-(2'-hydroxyethyl)aminoanisole sulfate |
| 0.020 g | 1,3-dihydroxybenzene |
| 0.040 g | 1,3-dihydroxy-2-methylbenzene |
| 0.008 g | 4-amino-3-methylphenol |
| 10.000 g | potassium oleate (8 percent aqueous solution) |
| 10.000 g | ammonia(22 percent aqueous solution) |
| 10.000 g | isopropanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 26

Hair Dye Composition

A hair dyeing solution having the following composition was prepared:

| | |
|---|---|
| 0.220 g | 2,5-diamino-1-(3-thienyl)benzene*2HCl |
| 0.100 g | 4-di(2-hydroxyethyl)aminoaniline sulfate |
| 0.020 g | 5-amino-2-methylphenol |
| 0.010 g | 1,3-diamino-4-(2-hydroxyethoxy)benzene |
| 0.015 g | 2-amino-4-(2'-hydroxyethyl)aminoanisole sulfate |
| 0.020 g | 1,3-dihydroxybenzene |
| 0.040 g | 1,3-dihydroxy-2-methylbenzene |
| 0.008 g | 4,5-diamino-1-(2-hydoxyethyl)-1H-pyrazole sulfate |
| 10.000 g | potassium oleate(8 percent aqueous solution) |
| 10.000 g | ammonia (22 percent aqueous solution) |
| 10.000 g | isopropanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 27

Hair Dye Composition

A hair dyeing solution having the following composition was prepared:

| | |
|---|---|
| 0.320 g | 2,5-diamino-1-(3-thienyl)benzene*2HCl |
| 0.020 g | 5-amino-2-methylphenol |
| 0.010 g | 1,3-diamino-4-(2-hydroxyethoxy)benzene |
| 0.015 g | 2-amino-4-(2'-hydroxyethyl)aminoanisole sulfate |
| 0.020 g | 1,3-dihydroxybenzene |
| 0.040 g | 1,3-dihydroxy-2-methylbenzene |
| 0.008 g | 4-amino-2-(aminomethyl)phenol dihydrochloride |
| 10.000 g | potassiuin oleate(8 percent aqueous solution) |
| 10.000 g | ammonia(22 percent aqueous solution) |
| 10.000 g | isopropanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Unless otherwise indicated all percentages are percentages by weight.

While the invention has been illustrated and described as embodied in new diaminobenzene derivative compounds and dye compositions containing same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A p-diaminobenzene derivative compound of the formula (I):

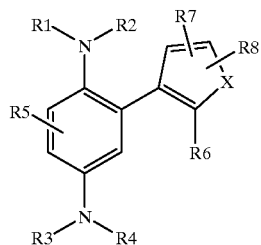

(I)

wherein X represents oxygen, sulfur, selenium or N-R9; R1, R2, R3 and R4 each, independently of each other, represents hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$)-alkyl group or R1 and R2 or R3 and R4 represent a four-membered to eight-membered aliphatic ring, with the proviso that at least 2 of the R1 to R4 groups represent hydrogen;

R5 represents hydrogen, a halogen atom, a $C_1$- to $C_4$-alkyl group, a $C_1$- to $C_4$-hydroxyalkyl group or a $C_1$- to $C_4$-alkoxy group;

R6 represents hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, an alkylamino group, a dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a C3- to $C_4$-dihydroxyalkyl group, a —CH=CHR10 group, a —(CH$_2$)$_p$—CO$_2$R11 group or a —(CH$_2$)$_p$R12 group with p=1, 2, 3 or 4, a —C(R13)=NR14 group or a —C(R16)H—NR17R18 group;

R7 and R8 each, independently of each other, represents hydrogen, a halogen atom, a cyano group, a hydroxy group, a $C_1$ - to $C_4$-alkoxy group, a $C_1$- to $C_6$-alkyl group, a $C_1$- to $C_4$-alkylthioether group, a mercapto group, a nitro group, an amino group, an alkylamino group, a dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydroxyalkyl group, a —CH=CHR10 group, a —(CH$_2$)$_p$—CO$_2$R11 group or a —(CH$_2$)$_p$R12 group with p=1, 2, 3 or 4, a —C(R13)=NR14 group or a —C(R16)H—NR17R18 group;

R9 represents hydrogen, a Ci- to $C_6$-alkyl group, a $C_1$- to $C_4$-hydroxyalkyl group, a phenyl group or an acetyl group;

R10 represents hydrogen, a hydroxy group, a nitro group, an amino group, a —CO$_2$R11 or a —C(O)CH$_3$ group;

R11, R13 and R16 each, independently of each other, represents hydrogen or a $C_1$- to $C_4$-alkyl group;

R12 represents an amino group or a nitrile group;

R14, R17 and R18 each, independently of each other, represents hydrogen, a hydroxy group, a $C_1$- to $C_4$-alkyl group, a $C_1$- to $C_4$-hydroxyalkyl group, a C3- to $C_4$-dihydroxyalkyl group or a group of formula (II):

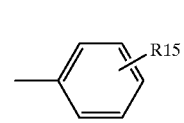

(II)

and R15 represents hydrogen, an amino group or a hydroxy group;

or a physiologically compatible salt thereof.

2. The p-diaminobenzene derivative compound as defined in claim 1, wherein one or more of said R5, R6, R7 and R8 represent said hydrogen.

3. The p-diaminobenzene derivative compound as defined in claim 1, wherein each of said R1, R2, R3 and R4 represent said hydrogen.

4. The p-diaminobenzene derivative compound as defined in claim 1, wherein said R7 represents said hydrogen and said R6 group represents said hydrogen, said —C(O)H group, said —C(O)CH$_3$ group, a $C_1$- to $C_4$-alkyl group, or said $C_1$- to $C_4$-hydroxyalkyl group.

5. The p-diaminobenzene derivative compound as defined in claim 4, wherein each of said R7 and R6 represent said hydrogen.

6. The p-diaminobenzene derivative compound as defined in claim 1, selected from the group consisting of 2,5-diamino-1-(5-chloro-3-thienyl)benzene, 2,5-diamino-1-(3-furyl)benzene, 2,5-diamino-1-(2-acetyl-3-thienyl)benzene, 2,5-diamino-1-(pyrrol-3-yl)benzene, 2,5-diamino-1-(2-formyl-3-thienyl)benzene, 2,5-diamino-1-(4-formyl-3-thienyl)-benzene, 2,5-diamino-1-(2-formyl-3-furyl) benzene, 2,5-diamino-1-(4-formyl-3-furyl)benzene, 2,5-diamino-1-(5-methyl-3-thienyl)-benzene, 2,5-diamino-1-(5-methyl-3-thienyl)benzene, 2,5-diamino-1-(4-(4-nitropropenyl)-3-thienyl)benzene, 2,5-diamino-1-(3-furyl) benzene, 2,5-diamino-1-(4-formyl-3-thienyl)benzene, 2,5-diamino-1-(4-(2-hydroxyethyl)amino-methyl-3-thienyl)-benzene, 2,5-diamino-1-(4-pyrrolidinomethyl-3-thienyl)-benzene, 2,5-diamino-1-(4-(dimethylaminoethyl) aminomethyl-3-thienyl)benzene, 2,5-diamino-1-(4-(2-methoxy-5-chloro-phenyl)aminomethyl-3-thienyl)benzene, 2,5-diamino-1-(4-(3-ethoxypropyl)aminomethyl-3-thienyl)-benzene, 2,5-diamino-1-(4-(methoxyethyl)-aminomethyl-3-thienyl)-benzene, 2,5-diamino-1-(4-(3,4-dimethoxyphenyl) aminomethyl-3-thienyl)-benzene, 2,5-diamino-1-(4-(4-trifluoromethyl-benzyl)aminomethyl-3-thienyl)benzene, 2,5-diamino-1-(4-(3-methoxyphenyl)aminomethyl-3-thienyl)benzene, 2,5-diamino-1-(4-(O,N-dimethylhydroxylaminomethyl-3-thienyl)benzene, 2,5-diamino-1-(4-(2,4-dimethoxy-5-chlorophenyl) aminomethyl-3-thienyl)benzene, 2,5-diamino-1-(4-(4-phenoxyphenyl)aminomethyl-3-thienyl)benzene, 2,5-diamino-1-(4-(2-diphenyl)aminomethyl-3-thienyl)benzene, 2,5-diamino-1-(4-(3,4-dimethoxybenzyl)aminomethyl-3-thienyl)benzene, 2,5-diamino-1-(4-(4-methoxyphenyl) aminomethyl-3-thienyl)benzene, 2,5-diamino-1-(4-(4-hydroxybutyl)aminomethy-1 -3-thienyl)-benzene, 2,5-diamino-1-(4-(2-methoxy-3-fluorophenyl)aminoraethyl-3-thienyl)benzene, 2,5-diamino-1-(4-(4-(1-phenylethyl) aminomethyl-3-thienyl)benzene, 2,5-diamino-1-(4-(2-furyl) aminomethyl-3-thienyl)benzene, 2,5-diamino-1-(4-(2-pyridyl)aminomethyl-3-thienyl)benzene, 2,5-diamino-1-(4-morpholinomethyl-3-thienyl)-benzene, 2,5-diamino-1-(4-(4-benzyl)pyperazinomethyl-3-thienyl)benzene, 2,5-diamino-1-(4-(3-carboxamidophenyl)aminomethyl-3-thienyl)benzene, 2,5-diamino-1-(4-(N-methyl-N-phenyl)-aminomethyl-3-thienyl)benzene, 2,5-diamino-1-(4-diethyl-aminomethyl-3-thienyl)benzene, 2,5-diamino-1-(4-(pyridin-4-yl-methyl)aminomethyl-3-thienyl)benzene, 2,5-diamino-1-(4-(3,5-dimethoxybenzyl)aminomethyl-3-thienyl)benzene, 2,5-diamino-1-(4-(4-morpholinophenyl) aminomethyl-3-thienyl)-benzene, 2,5-diamino-1-(4-(1-(2-hydroxyethyl))propyl-aminomethyl-3-thienyl)benzene, 2,5-diamino-1-(4-cyclopropyl-aminomethyl-3-thienyl)benzene, N-(2-{ [4-(2,5-diaminophenyl)-thiophen-2-yl-methyl]-amino)ethyl)acetamide, 2,5-diamino-1-(4-cyclohexylaminomethyl-3-thienyl)benzene, 2,5-diamino-1-(4-propylaminomethyl-3-thienyl)benzene, 2,5-diamino-1-(4-(o-tolyl)aminomethyl-3-thienyl)benzene, 2,5-diamino-1-(4-(N-methyl-N-cyclohexyl)aminomethyl-3-thienyl) benzene, 2,5-diamino-1-(4-(2,6-dimethylmorpholino) methyl-3-thienyl)benzene, 2,5-diamino-1-(4-(3,5-dimethylpiperidino)methyl-3-thienyl)benzene, 2,5-diamino-1-(4-(3-(1-hydroxyethyl)-phenyl)-aminomethyl-3-thienyl) benzene, 2,5-diamino-1-(4-(3,4-dimaethyl-phenyl) aiminomethyl-3-thienyl)benzene, 2,5-diamino-1-(4-(3-methylmercaptophenyl)aminomethyl-3 -thienyl)benzene, 2,5-diamino-1-(4-(4-diphenyl)aminomethyl-3-thienyl) benzene, 2,5-diamino-1-(4-(4-isopropylphenyl) aminomethyl-3-thienyl)benzene, 2,5-diamino-1-(4-pentyl-aminomethyl-3-thienyl)benzene, 2,5-diamino-1-(4-(dibutyl) aminomethyl-3-thienyl)benzene, 2,5-diamino-1-(4-isopropyl-aminomethyl-3-thienyl)benzene, 2,5-diamino-1-(4-(N-cyclopropylmethyl-N-propyl)aminomethyl-3-thienyl) benzene, 2,5-diamino-1-(4-(4-hydroxy)piperidinomethyl-3-thienyl)benzene, 2,5-diamino-1-(4-(fluorenyl)aminomethyl-3-thienyl)benzene, 2,5-diamino-1-(4-(4-dimethylaminophenyl)-aminomethyl-3-thienyl)benzene, 2,5-diamino-1-(4-(3,5-dimethylphenyl)aminomethyl-3-thienyl)benzene, 2,5-diamino-1-(4-(4-methoxybenzyl) aminomethyl-3-thienyl)benzene, 2,5-diamino-1-(4-(indanyl)-aminomethyl-3-thienyl)benzene, 2,5-diamino-1-(4-(3-fluorobenzyl)aminomethyl-3-thienyl)-benzene, 2,5-diamino-1-(4-(benzyl)aminomethyl-3-thienyl)-benzene, 2,5-diamino-1-(4-(4-methylpiperazino)aminomethyl-3-thienyl)benzene, 2,5-diamino-1-(4-(4-tert-butylphenyl)-aminomethyl-3-thienyl)benzene, 2,5-diamino-1-(4-(2-chloro-benzyl)aminomethyl-3-thienyl)benzene, 2,5-diamino-1-(4-(naphth-1-yl-methyl)aminomethyl-3-thienyl) benzene, 2,5-diamino-1-(4-(phenyl)aminomethyl-3-thienyl) benzene, 2,5-diamino-1-(4-(4-chlorophenyl)aminomethyl-3-thienyl)benzene, 4-{[4-(2,5-diaminophenyl)thiophen-2-yl-methyl]amino}benzoic acid methyl ester and 2,5-diamino-1-(3-thienyl)benzene.

7. A dye composition for oxidative dyeing of keratin fibers, said dye composition containing a combination of coupler and developer substances, said developer substance comprising at least one p-diaminobenzene derivative compound of the formula (I):

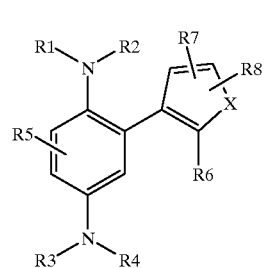

(I)

wherein X represents oxygen, sulfur, selenium or N-R9;
R1, R2, R3 and R4 each, independently of each other, represents hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$)-alkyl group or R1 and R2 or R3 and R4 represent a four-membered to eight-membered aliphatic ring, with the proviso that at least 2 of the R1 to R4 groups represent hydrogen;
R5 represents hydrogen, a halogen atom, a $C_1$- to $C_4$-alkyl group, a $C_1$- to $C_4$-hydroxyalkyl group or a $C_1$- to $C_4$-alkoxy group;
R6 represents hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, an alkylamino group, a dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydroxyalkyl group, a —CH═CHR10 group, a —(CH$_2$)$_p$—CO$_2$R11 group or a —(CH$_2$)$_p$R12 group with p=1, 2, 3 or 4, a —C(R13)═NR14 group or a —C(R16)H—NR17R18 group;
R7 and R8 each, independently of each other, represents hydrogen, a halogen atom, a cyano group, a hydroxy group, a $C_1$- to $C_4$-alkoxy group, a $C_1$- to $C_6$-alkyl group, a $C_1$- to $C_4$-alkylthioether group, a mercapto group, a nitro group, an amino group, an alkylamino group, a dialkylamino group, a —C(O)H group, a —C(O)CH₃ group, a —C(O)CF₃ group, a —Si(CH₃)₃ group, a C₁- to C₄-hydroxyalkyl group, a C₃- to C₄-dihydroxyalkyl group, a —CH═CHR10 group, a —(CH₂)$_p$—CO₂R11 group or a —(CH₂)$_p$R12 group with p=1, 2, 3 or 4, a —C(R13)═NR14 group or a —C(R16)H—NR17R18 group;

R9 represents hydrogen, a C₁- to C₆-alkyl group, a C₁- to C₄-hydroxyalkyl group, a phenyl group or an acetyl group;

R10 represents hydrogen, a hydroxy group, a nitro group, an amino group, a —CO₂R11 or a —C(O)CH₃ group;

R11, R13 and R16 each, independently of each other, represents hydrogen or a C₁- to C₄-alkyl group;

R12 represents an amino group or a nitrile group;

R14, R17 and R18 each, independently of each other, represents hydrogen, a hydroxy group, a C₁- to C₄-alkyl group, a C₁- to C₄-hydroxyalkyl group, a C₃- to C₄-dihydroxyalkyl group or a group of formula (II):

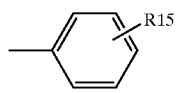

(II)

and R15 represents hydrogen, an amino group or a hydroxy group, or a physiologically compatible salt thereof.

8. The composition as defined in claim 7, containing from 0.005 to 20.0 percent by weight of said at least one p-diaminobenzene derivative compound or said salt.

9. The composition as defined in claim 7, wherein said coupler substance is selected from the group consisting of 2,6-diaminopyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxy-benzene, 2,3-diamino-6-methoxypyridine, 3-amino-6-methoxy-2-(methylamino) pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di-(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di-(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethylamino]aniline, 3-[(2-aminoethyl)amino]aniline, 1,3-di(2,4-diaminophenoxy)propane, di(2,4-diaminophenoxy)-methane, 1,3-diamino-2,4-dimethoxybenzene, 2,6-bis-(2-hydroxyethyl)aminotoluene,4-hydroxyindole, 3-dimethylamino-phenol, 3-diethylaminophenol, 5-amino-2-methylphenol, 5-amino-4-fluoro-2-methylphenol, 5-amino-4-methoxy-2-methyl-phenol, 5-amino-4-ethoxy-2-methyl-phenol, 3-amino-2,4-dichlorophenol, 5-amino-2,4-dichlorophenol,3-amino-2-methyl-phenol, 3-amino-2-chloro-6-methylphenol, 3-aminophenol, 2-[(3-hydroxyphenyl)amino]acetamide, 5-[(2-hydroxyethyl)-amino]-2-methylphenol, 3-[(2-hydroxyethyl)amino]phenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalin, 2-methyl-1-naphthol acetate, 1,3-dihydroxybenzene, 1-chloro-2,4-dihydroxybenzene, 2-chloro-1,3-dihydroxybenzene, 1,2-dichlor-3,15-dihydroxy-4-methylbenzene, 1,5-dichloro-2,4-dihydroxybenzene, 1,3-dihydroxy-2-methylbenzene, 3,4-methylendioxyphenol, 3,4-methylendioxy-aniline, 5-[(2-hydroxyethyl)amino]-1,3-benzodioxol, 6-bromo-1-hydroxy-3,4-methylendioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindolene, 5-hydroxyindole, 6-hydroxyindole, 7-hydroxyindole and 2,3-indolindione.

10. The composition as defined in claim 7, wherein said developer substance contains at least one member selected from the group consisting of 1,4-diaminobenzene, 2,5-diaminotoluene, 2,5-diaminophenylethyl alcohol, 4-aminophenol, substituted 4-aminophenols, substituted 4,5-diaminopyrazoles and tetraaminopyrimidines.

11. The composition as defined in claim 7, containing a total amount of 0.005 to 20 percent by weight of said developer substance and said coupler substance.

12. The composition as defined in claim 7, further comprising at least one direct-dyeing dye compound.

13. The composition as defined in claim 12, wherein said at least one direct-dyeing dye compound is selected from the group consisting of triphenylmethylene dye compounds, aromatic nitro dye compounds, azo dye compounds and dispersion dye compounds.

14. The composition as defined in claim 7, having a pH of from 6.8 to 11.5.

15. The composition as defined in claim 7, in the form of an aqueous or aqueous-alcoholic solution, a cream, a gel or an emulsion.

16. The composition as defined in claim 7, further comprising at least one cosmetic additive ingredient appropriate for hair dyeing compositions.

17. The composition as defined in claim 16, wherein said at least one cosmetic additive ingredient is selected from the group consisting of solvents, wetting agents, emulsifiers, thickeners, hair care materials, antioxidants, perfumes and complexing agents.

* * * * *